United States Patent
Ortiz-Marciales et al.

(10) Patent No.: US 8,012,901 B1
(45) Date of Patent: Sep. 6, 2011

(54) METHOD OF SYNTHESIZING ENANTIOPURE MEXILETINE ANALOGUES AND NOVEL β-THIOPHENOXY AND PYRIDYL ETHERS

(76) Inventors: Margarita Ortiz-Marciales, Humacao, PR (US); Kun Huang, Corvallis, OR (US); Viatcheslav Stepanenko, Humacao, PR (US); Melvin De Jesus, Humacao, PR (US); Wildeliz Correa, Humacao, PR (US)

( * ) Notice: Subject to any disclaimer, the term of this patent is extended or adjusted under 35 U.S.C. 154(b) by 176 days.

(21) Appl. No.: 12/386,356

(22) Filed: Apr. 15, 2009

Related U.S. Application Data

(63) Continuation-in-part of application No. 11/512,599, filed on Aug. 30, 2006.

(51) Int. Cl.
| | |
|---|---|
| *B01J 21/00* | (2006.01) |
| *B01J 23/00* | (2006.01) |
| *B01J 25/00* | (2006.01) |
| *B01J 29/00* | (2006.01) |
| *B01J 31/00* | (2006.01) |
| *B01J 21/02* | (2006.01) |
| *B01J 21/04* | (2006.01) |
| *B01J 23/02* | (2006.01) |

(52) U.S. Cl. ......... 502/100; 502/150; 502/202; 502/439
(58) Field of Classification Search .............. 502/100, 502/150, 202, 439
See application file for complete search history.

(56) References Cited

OTHER PUBLICATIONS

Liu et al., Heletica CHimica Acta, vol. 87 (2004) pp. 2310-2317.*

* cited by examiner

*Primary Examiner* — James E McDonough
(74) *Attorney, Agent, or Firm* — Holglund & Pamias, PSC; Roberto J. Rios

(57) ABSTRACT

A practical and efficient procedure for the enantioselective synthesis of mexiletine analogues using 10% of a novel spiroborate ester as chirality transfer agent is presented. A variety of mexiletine analogues were prepared with excellent enantioselectivities (91-97% ee) in good yield from readily available starting materials. The developed methodology was also successfully applied for the synthesis of novel β-amino ethers containing thiophenyl and pyridyl fragments.

33 Claims, 3 Drawing Sheets

R= Me, Aryl
X= Br, Cl

Y = O, S
Ar = Aryl, Py up to 97% ee

METHOD OF SYNTHESIZING ENANTIOPURE MEXILETINE ANALOGUES AND NOVEL β-THIOPHENOXY AND PYRIDYL ETHERS

CROSS-REFERENCE TO RELATED APPLICATIONS

This application is a continuation-in-part of U.S. patent application Ser. No. 11/512,599, filed on Aug. 30, 2006, still pending. The entirety of this application is incorporated herein by reference.

GOVERNMENT INTEREST

The claimed invention was made with U.S. Government support under grant numbers MBRS GM 08216 and NIH-INBRE NC P20 RR-016470 awarded by the National Institute of Health (NIH). The government has certain rights in this invention.

BACKGROUND OF THE INVENTION

Mexiletine (FIG. 1a) is an effective sodium channel blocker used as an antiarrhythmic and analgesic oral drug. Structure-activity studies in vivo and in vitro of pharmacologically active mexiletine indicate that its (−)-(R) enantiomer binds preferentially to the cardiac sodium channels. In addition, (−)-(R)-mexiletine is also more active than (+)-(S)-mexiletine on native skeletal muscular fibers. The use of mexiletine as a racemate in the treatment of neuromuscular disorders is limited due to its possible side effects. As shown in FIG. 1b, the optically active mexiletine analogue (R)-2 is 27-fold more potent than (R)-mexiletine in producing a tonic block and 23-fold more potent in condition of high frequency of stimulation (phasic block). Recently, racemate (3) shown in FIG. 1c was established as a novel potent blocker of voltage-gated $K^+$ channels using structure-based virtual screening in conjunction with electrophysiological assays in rat hippocampal neurons.

The preparation of mexiletine enantiomers has been reported previously by several groups. Generally, the methods involved resolution of racemic intermediates, enzymatic hydrolysis of an N-acyl derivative, or using a stereospecific, four-step procedure, in 7.2% overall yield. Flippin, et al. reported a convenient procedure for the preparation of stereoisomers of mexiletine, but the scope of products was limited by the availability of chiral substrates and expensive chromium tricarbonyl complexes of aryl halides: hence, some amines were provided in the racemate form. Although Franchini et al. synthesized the stereoisomers of mexiletine analogues, the use of 2-phenyl-oxirane as chiral source restricted the range of mexiletine analogues. Furthermore, the procedure is also controlled by the regio-specificity of the ring-opening reaction, and the possible racemization of the benzylic carbon by the substitution of the alkoxy group by the amine. Hence, a practical and efficient route for the synthesis of highly enantiopure mexiletine analogues is highly desirable.

SUMMARY OF THE INVENTION

According to one aspect of the invention, a practical and efficient procedure for the enantioselective synthesis of mexiletine analogues using a novel spiroborate ester as chirality transfer agent is presented. Moreover, 10% of the spiroborate is used for the synthesis.

In another aspect of the invention, a variety of mexiletine analogues were prepared in good yield with excellent enantioselectivities (91%-97% ee) from readily available starting materials.

According to a further aspect of the invention, the developed methodology was applied for the synthesis of novel β-amino ethers containing thiophenyl and pyridyl fragments.

According to another aspect of the invention, a method of synthesizing enantiopure mexiletine analogues and novel β-thiophenoxy and pyridyl ethers is performed by reducing an O-benzyl oxime in the presence of a novel catalyst agent.

According to one aspect of the invention, the catalyst agent is able to reduce said oxime to obtain an enantioselectivity of at least 91%.

According to another aspect of the invention, the catalyst agent is able to reduce said oxime to obtain an enantioselectivity of from about 91% to about 97%.

BRIEF DESCRIPTION OF THE DRAWINGS

Further features and advantages of the invention will become apparent from the following detailed description taken in conjunction with the accompanying figures showing illustrative embodiments of the invention, in which.

Throughout the figures, the same reference numbers and characters, unless otherwise stated, are used to denote like elements, components, portions or features of the illustrated embodiments. The subject invention will be described in detail in conjunction with the accompanying figures, in view of the illustrative embodiments.

DETAILED DESCRIPTION OF THE INVENTION

Figure 1:
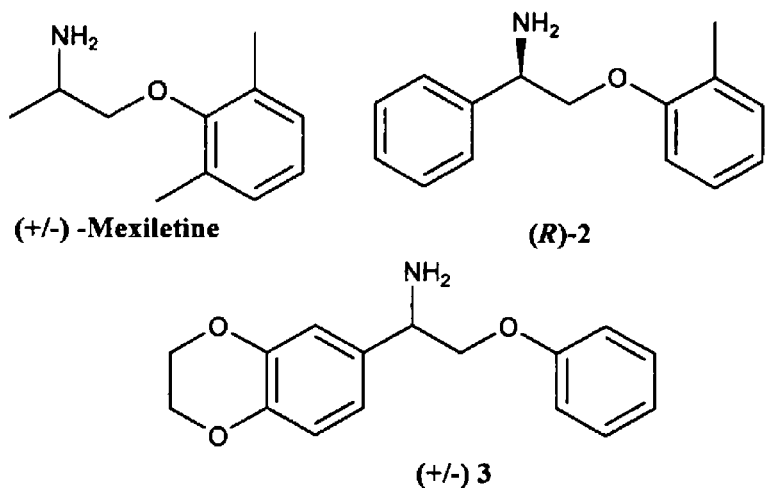
FIG. 1 shows Mexiletine and examples of its more potent analogues.
Figure 2:
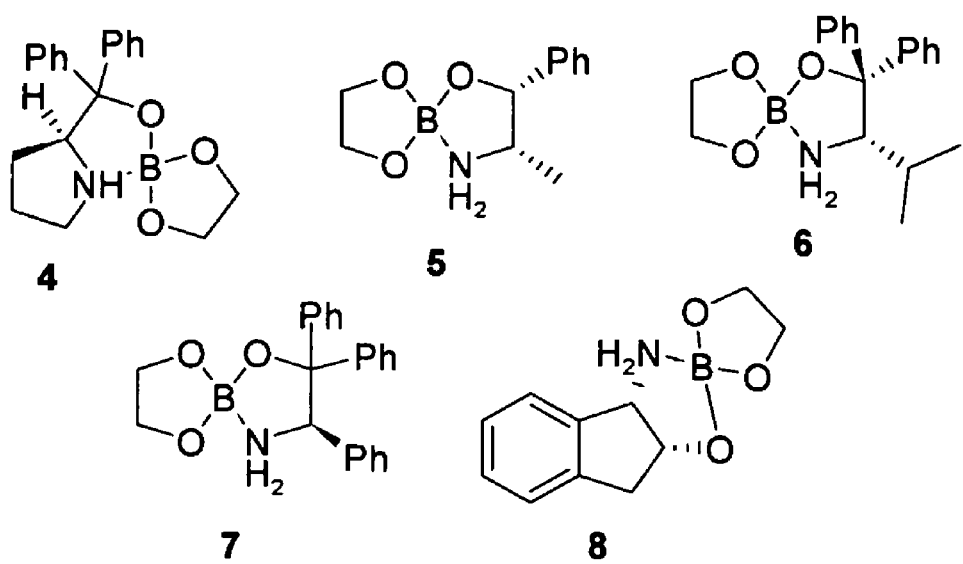
FIG. 2 shows spiroborate esters derived from nonracemic aminoalcohols and ethylene glycol according to the invention.

The inventors of the present invention have been successful in the borane-mediated asymmetric reduction of O-benzyl oximes using a truly catalytic amount of air and moisture stable spiroborate esters as shown in FIG. 2 and disclosed in the above-referenced related application incorporated in its entirety herein by reference. Thus, the present invention discloses its application for the enantioselective synthesis of β-amino ethers of biological interest.

Figure 3:
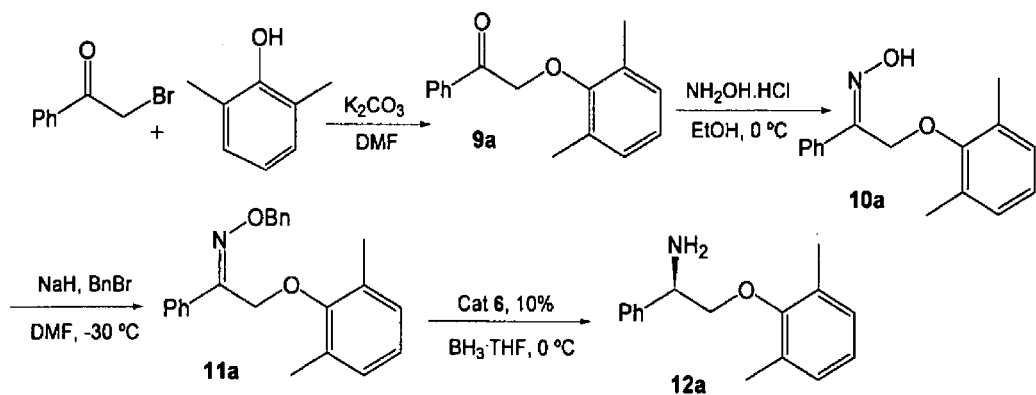
FIG. 3 shows a scheme for the synthesis of a Mexiletine analogue according to the invention.

The synthesis of Mexiletine analogue 12a, as outlined in FIG. 3, was selected as a model protocol. The aryloxy acetophenone 9a was prepared from the 2-chloro- or 2-bromoacetophenone using different bases (NaOH, NaH and $K_2CO_3$). After optimization, it was found that treatment of 2-bromoacetophenone with $K_2CO_3$ (1.5 equiv) and 2,6-dimethylphenol (1.5 equiv) in DMF at room temperature for 24 h gave the desired ketone in 81% yield. The oxime was then prepared by addition of $NH_2OH.HCl$ and pyridine at 0° C. The mixture of (Z)- and (E)-isomers was easily separated by simple recrystallization. The main (Z)-benzyl oxime ether 11a was obtained in high yield from pure (Z)-oxime using NaH and benzyl bromide in DMF at −30° C.

Initially, the spiroborates shown in FIG. 2 were screened for the reduction of the O-benzyl oxime 11a. The reactivity of catalysts 5, 7 and 8 was rather low at 0° C. The complete conversion was achieved at room temperature (22° C.) affording 57%, 81% and 82% ee, respectively. Spiroborate ester 6 provided the best enantioselectivities. Table 1 below summarizes these results.

TABLE 1

Screening of Different Catalysts for the Reduction of 11a.

| catalyst | temp (° C.) | catalyst equiv | yield (%)$^a$ | ee (%)$^b$ |
|---|---|---|---|---|
| 4 | 0 | 0.10 | 87 | 70 (R) |
| 5 | 22 | 0.10 | 40 | 57 (R) |
| 6 | 0 | 0.10 | 84 | 97 (R) |
| 6 | 0 | 0.25 | 92 | 99 (R) |
| 7 | 22 | 0.10 | 80 | 81 (S) |
| 8 | 22 | 0.10 | 76 | 82 (S) |

Under the optimized conditions, a variety of O-benzyl oximes were prepared and reduced in dioxane employing 10% spiroborate ester 6 and 4 equiv BH3.THF at 0° C. Table 2 below illustrates the results for various O-benzyl oximes that were reduced to the enantiopure amines in 91-97% ee, and in good to excellent isolated yield. Noteworthy, (R)-mexiletine was prepared in 94% ee and 84% chemical yield (entry 2), illustrating, clearly, the reagent ability to differentiate between the methyl and the alkoxy moiety in the borane-catalyzed reduction. Generally, substituents on each aryl groups influenced slightly the enantioselectivities (entries 3-11). For example, O-benzyl oximes bearing both electron-withdrawing and electron-donating aryl groups provided higher enantioselectivities (entry 3 and 6). The absolute configuration of products was determined by comparing the optical rotations with the corresponding known compounds.

TABLE 2

Asymmetric Reduction of Representative Oxime Benzyl Ethers with 0.1 Equivalent of Catalyst 6.

| entry 12 | | [α] D$^a$ | yield (%)$^b$ | ee (%)$^c$ |
|---|---|---|---|---|
| 1 | a | −28 (1.2) | 84 | 97$^d$ |
| 2 | b | −66 (1.0) | 84 | 94$^e$ |
| 3 | c | −19 (1.9) | 89 | 97 |
| 4 | d | −47 (1.5) | 82 | 92 |
| 5 | e | −36 (1.2) | 73 | 94 |

TABLE 2-continued

Asymmetric Reduction of Representative Oxime Benzyl Ethers with 0.1 Equivalent of Catalyst 6.

| entry 12 | [α] D[a] | yield (%)[b] | ee (%)[c] |
|---|---|---|---|
| 6 f | −17 (1.0) | 85 | 95[d] |
| 7 g | −43 (1.2) | 74 | 92 |
| 8 h | −47 (2.4) | 91 | 93[d] |
| 9 i | −38 (1.2) | 89 | 93 |
| 10 j | −36 (1.0) | 83 | 94 |
| 11 k | −25 (1.2) | 86 | 91 |

[a]$CHCl_3$ as solvent.
[b]Isolated yield of amine
[c]Determined by amine on chiral HPLC (Chiralcel OD-H column).
[d]Determined by acetyl derivative on Chiralcel OD-H column.
[e]Determined by GC of acetyl derivative on Chiral column (CP-Chirasil-DexCB).

Figure 4:
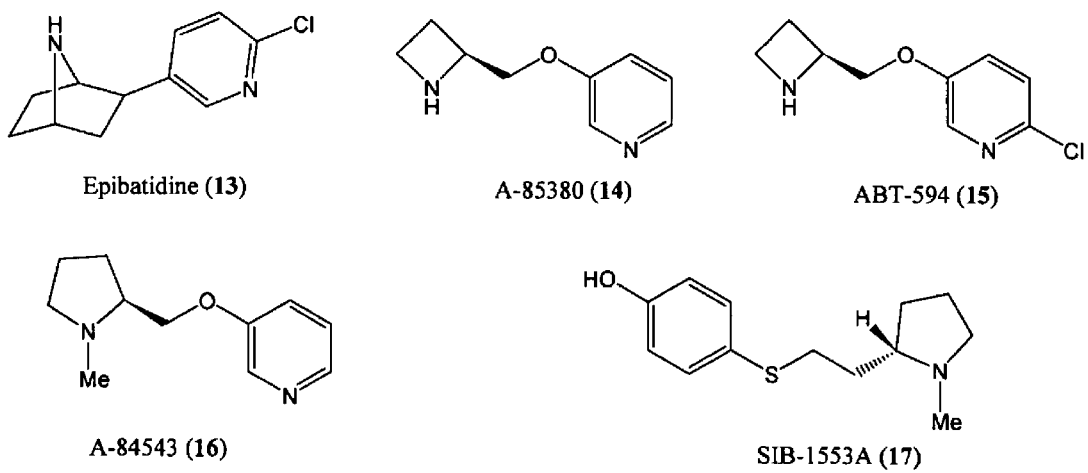
FIG. 4 shows several neuronal nicotinic acetylcholine receptors agonist.
Figure 5:
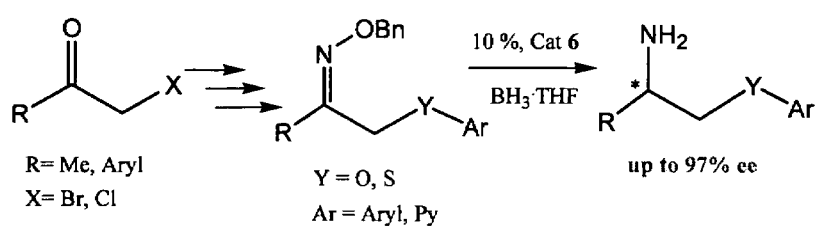
FIG. 5 shows the procedure for the enantioselective synthesis of mexiletine analogues using a novel chirality transfer agent according to the invention.
Figure 5:
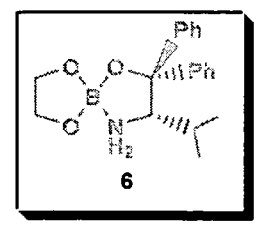

Our efforts in the design of novel neuronal Nicotinic Acetylcholine Receptors (nAChRs) agonists, led us to target enantiopure arylamino ethers as therapeutic agents for the treatment of CNS and peripheral nervous system disorders. Within the past ten years, a series of selective agonist of human neuronal nAChRs, such as Epibatidine (13), A-85380 (14), ABT-594 (15), A-84543 (16), and SIB-1553A (17) as shown in FIG. 4, has been found. Additionally, compounds containing fluorine are widely applied in the fields of agricultural, medicinal and material chemistry, especially fluorinated aromatics which are widely found in many modern drugs.

Based on similar structural features present in nAChRs agonists, highly enantiopure fluorinated benzylic primary amines with β-thiophenoxy and pyridyloxy groups of biologically significance, were prepared using the previous procedure with excellent enantioselectivity (94-97% ee) in good yield, as shown in Table 3 below.

TABLE 3

Asymmetric Synthesis of Novel Amines with 0.1 Equivalents of Catalyst 6.

| entry 12 | | $[\alpha]_D{}^a$ | yield (%)[b] | ee (%)[c] |
|---|---|---|---|---|
| 1 | (structure l) | +35 (1.3) | 86 | 96 |
| 2 | (structure m) | +26 (1.2) | 72 | 94 |
| 3 | (structure n) | −11 (1.4) | 66 | 97 |
| 4 | (structure o) | −36 (2.1) | 83 | 97[d] |
| 5 | (structure p) | −23 (3.5) | 84 | 96 |

[a]CHCl₃ as solvent.
[b]Isolated yield of amine.
[c]Determined by chiral HPLC (Chiralcel OD-H column).
[d]Determined by P NMR analysis of the phosphonate derivative.

A general procedure for the reduction according to the invention will be explained.

I. General Procedures

Catalysts, 2-Bromo-1-(2,3-dihydrobenzol[b]-[1,4]-dioxin-6-yl)-ethanone were synthesized according to literature procedures. Air and moisture sensitive reactions were carried out in dried glassware under N₂ atmosphere. Common solvents were dried and distilled by standard procedures. All reagents were obtained commercially unless otherwise noted. Chromatographic purification of products was accomplished using flash chromatography on silica gel Si 60 Å (200-400 mesh).

H, C and B spectra were recorded on a 400 MHz spectrometer with standard pulse sequences operating at 400.152 MHz, 100.627 MHz, and 128.384 MHz for H, C and B respectively. Chiral gas chromatography analysis was processed using a Chrompack Chiralsil-Dex-CB column (30 m×0.25 mm×0.25 μm). GC-MS analysis was processed on a GC/Polaris Q Mass detector using a Restek RTX-5MS column. Chiral HPLC analysis was processed with an OD-H column.

II Experimental Procedures and Characterizations:

1. General Procedure for the Preparation of Ketones

To a 100 mL round bottom flask charged with magnetic stirrer, 2-bromoacetophenone (1.99 g, 10 mmol), 2,6-dimethylphenol (15 mmol) and K₂CO₃ (15 mmol) was added 20 mL DMF and the resulting mixture was stirred for 24 h at room temperature. The reaction was quenched with 50 mL H₂O and the aqueous phase was extracted with diethyl ether (3×40 mL). The combined organic phase was washed with 2 N NaOH (2×20 mL) to remove the excess of phenol, dried over MgSO₄ and concentrated under reduced pressure. The residue was purified by flash column chromatography on silica gel.

2-(2,6-Dimethyl-phenoxy)-1-phenyl-ethanone (9a)

Purified by silica gel/hexane:ethyl acetate (5:1) column chromatography as a yellow solid; mp 57-59° C., lit. 60-61° C.; yield 81% (1.94 g); H NMR (400 MHz, CDCl$_3$): d 2.23 (s, 6H, CH$_3$), 5.02 (s, 2H, OCH$_2$), 6.89 (m, 1H, Ar), 6.97 (m, 2H, Ar), 7.41 (m, 2H, Ph), 7.52 (m, 1H, Ph), 7.90 (m, 2H, Ph); CNMR (100 MHz, CDCl$_3$): δ 16.3, 74.5, 124.5, 127.9, 128.8, 129.0, 130.8, 133.7, 134.7, 155.7, 194.1; GC-MS m/z 240.2 (M$^+$).

1-(2,6-Dimethyl-phenoxy)-propan-2-one (9b)

Prepared by 1-chloro-propan-2-one (50 mmol) and 2,6-dimenthylphenol (60 mmol); purified by silica gel/hexane: ethyl acetate (5:1) column chromatography as a colorless oil; yield 84% (7.5 g); H NMR (400 MHz, CDCl$_3$): d 2.34 (s, 6H, CH$_3$), 2.42 (s, 3H, CH$_3$), 4.40 (s, 2H, OCH$_2$), 7.02-7.10 (m, 3H, Ar); CNMR (100 MHz, CDCl$_3$): δ 16.3, 26.6, 76.8, 124.5, 129.1, 130.6, 155.0, 205.4; GC-MS m/z 178.1 (M$^+$).

2-(2,6-Dimethyl-phenoxy)-1-(4-fluoro-phenyl)-ethanone (9c)

Purified by silica gel/hexane:ethyl acetate (5:1) column chromatography as a colorless oil; yield 77% (1.95 g); H NMR (400 MHz, CDCl$_3$): d 2.35 (s, 6H, CH$_3$), 5.10 (s, 2H, OCH$_2$), 7.01-7.10 (m, 3H, Ar), 7.22 (m, 2H, Ar), 8.08 (m, 2H, Ar); CNMR (100 MHz, CDCl$_3$): δ 16.3, 74.5, 115.9 (d), 124.6, 128.6, 129.1, 131.1 (m), 155.6, 164.8, 167.4, 192.7; GC-MS m/z 258.1 (M$^+$).

1-(4-Fluoro-phenyl)-2-o-tolyloxy-ethanone (9d)

Purified by silica gel/hexane:ethyl acetate (5:1) column chromatography as a colorless oil; yield 86% (2.1 g); H NMR (400 MHz, CDCl$_3$): d 2.34 (s, 3H, CH$_3$), 5.26 (s, 2H, OCH$_2$), 6.79 (m, 1H, Ar), 6.96 (m, 1H, Ar), 7.16-7.24 (m, 4H, Ar), 8.12 (m, 2H, Ar); CNMR (100 MHz, CDCl$_3$): δ 16.3, 71.3, 111.3, 115.9, 121.5, 126.9, 127.2, 131.1, 131.2 156.1, 164.9, 167.4, 193.8; GC-MS m/z 244.1 (M$^+$).

1-(4-Chloro-phenyl)-2-o-tolyloxy-ethanone (9e)

Purified by silica gel/hexane:ethyl acetate (5:1) column chromatography as a yellow solid; mp 61-62° C.; yield 83% (2.15 g); H NMR (400 MHz, CDCl$_3$): d 2.33 (s, 3H, CH$_3$), 5.25 (s, 2H, OCH$_2$), 6.79 (m, 1H, Ar), 6.96 (m, 1H, Ar), 7.16-7.23 (m, 2H, Ar), 7.51 (m, 2H, Ar), 8.03 (m, 2H, Ar); CNMR (100 MHz, CDCl$_3$): δ 16.3, 71.3, 111.3, 121.5, 126.9, 127.2, 129.1, 129.9, 131.1, 133.1, 140.3, 156.1, 194.2; GC-MS m/z 260.1 (M$^+$).

1-(4-Chloro-phenyl)-2-(2,6-dimethyl-phenoxy)-ethanone (9f)

Purified by silica gel/hexane:ethyl acetate (5:1) column chromatography as a colorless oil; yield 79% (2.17 g); H NMR (400 MHz, CDCl$_3$): d 2.35 (s, 6H, CH$_3$), 5.11 (s, 2H, OCH$_2$), 7.02-7.10 (m, 3H, Ar), 7.52 (m, 2H, Ar), 7.99 (m, 2H, Ar), CNMR (100 MHz, CDCl$_3$): δ 16.3, 74.5, 124.6, 129.1, 129.2, 129.5, 130.7, 133.0, 140.3, 155.6, 193.2; IR ν (cm$^{-1}$) 3486, 3031, 2925, 2919, 2857, 1702, 1589, 1572, 1476, 1401, 1265, 1227, 1195, 1177, 1091, 1013, 972, 852, 767; GC-MS m/z 274.1 (M$^+$); ESI HRMS m/z calcd for O$_{16}$H$_{16}$O$_2$$_{01}$ (M+H)$^+$ 275.08337, found 275.08328.

2-(2-Chloro-phenoxy)-1-(4-chloro-phenyl)-ethanone (9g)

Purified by silica gel/hexane:ethyl acetate (5:1) column chromatography as a yellow solid; mp 97-98° C., lit. 108.5; yield 91% (2.55 g); H NMR (400 MHz, CDCl$_3$): d 5.32 (s, 2H, OCH$_2$), 6.93 (m, 1H, Ar), 7.00 (m, 1H, Ar), 7.23 (m, 1H, Ar), 7.45 (m, 1H, Ar), 7.52 (d, 2H, J=8.4 Hz, Ar), 8.06 (d, 2H, J=8.4 Hz, Ar); CNMR (100 MHz, CDCl$_3$): δ 72.1, 114.1, 122.7, 123.4, 127.8, 129.2, 129.9, 130.7, 132.8, 140.6, 153.6, 193.4; GC-MS m/z 280.0 (M$^i$).

1-Phenyl-2-o-tolyloxy-ethanone (9h)

Purified by silica gel/hexane:ethyl acetate (5:1) column chromatography as yellow solid; mp 60-61° C., lit. 60-61° C.; yield 89% (3.85 g); H NMR (400 MHz, CDCl$_3$): d 2.35 (s, 3H, CH$_3$), 5.31 (s, 2H, OCH$_2$), 6.80 (m, 1H, Ar), 6.95 (m, 1H, Ar), 7.16-7.23 (m, 2H, Ar), 7.55 (m, 2H, Ar), 7.67 (m, 1H, Ar), 8.06 (m, 2H, Ar); CNMR (100 MHz, CDCl$_3$): δ 16.3, 71.2, 111.4, 121.4, 126.8, 127.3, 128.3, 128.8, 131.1, 133.8, 134.8, 156.3, 195.0; GC-MS m/z 226.2 (M$^+$).

2-(4-Chloro-phenoxy)-1-phenyl-ethanone (9I)

Purified by silica gel/hexane:ethyl acetate (5:1) column chromatography as yellow solid; mp 95-97° C.; yield 87% (4.28 g); H NMR (400 MHz, CDCl$_3$): d 5.31 (s, 2H, OCH$_2$), 6.91 (m, 2H, Ar), 7.30 (m, 2H, Ar), 7.54 (m, 2H, Ar), 7.68 (m, 1H, Ar), 8.03 (m, 2H, Ar); CNMR (100 MHz, CDCl$_3$): δ 71.0, 116.2, 126.7, 128.1, 128.9, 129.5, 134.0, 134.5, 156.7, 194.1; GC-MS m/z 246.1 (M$^+$).

1-(2,3-Dihydro-benzo-[1,4]-dioxin-6-yl)-2-phenoxy-ethanone (9j)

Purified by crystallization as a brown solid; mp 82-83° C.; yield 92% (1.98 g); H NMR (400 MHz, CDCl$_3$): d 4.33 (m, 2H, OCH$_2$), 4.37 (m, 2H, OCH$_2$), 5.24 (s, 2H, OCH$_2$), 7.00 (m, 4H, Ar), 7.33 (m, 2H, Ar), 7.61 (m, 2H, Ar); CNMR (100 MHz, CDCl$_3$): δ 64.1, 64.8, 70.7, 114.9, 117.5, 117.7, 121.6, 122.4, 128.4, 129.6, 143.6, 148.7, 158.1, 192.9; GC-MS m/z 269.9 (M$^+$).

1-(2,3-Dihydro-benzo-[1,4]-dioxin-6-yl)-2-o-tolyloxy-ethanone (9k)

Purified by silica gel/hexane:ethyl acetate (3:1) column chromatography as a brown solid; mp 94-96° C.; yield 85% (2.4 g); H NMR (400 MHz, CDCl$_3$): d 2.36 (s, 3H, CH$_3$), 4.33 (m, 2H, OCH$_2$), 4.38 (m, 2H, OCH$_2$), 5.23 (s, 2H, OCH$_2$), 6.78 (m, 1H, Ar), 6.97 (m, 2H, Ar), 7.18 (m, 2H, Ar), 7.63 (m, 2H, Ar); CNMR (100 MHz, CDCl$_3$): δ 16.4, 64.1, 64.8, 71.1, 111.4, 117.4, 117.9, 121.3, 122.5, 126.8, 127.2, 128.5, 131.0, 143.5, 148.6, 156.3, 193.4; IR ν (cm$^{-1}$) 2940, 2919, 2887, 1685, 1604, 1579, 1509, 1493, 1464, 1283, 1262, 1233, 1222, 1168, 1114, 1064, 982, 901, 814, 763, 748; GC-MS m/z 284.2 (M$^+$); ESI HRMS m/z calcd for C$_{17}$H$_{17}$O$_4$ (M+H)$^+$ 285.11214, found 285.11194.

2-(4-Methoxy-phenylsulfanyl)-1-phenyl-ethanone (9l)

Purified by silica gel/hexane:ethyl acetate (4:1) column chromatography as a slightly yellow oil; yield 76% (1.85 g); H NMR (400 MHz, CDCl$_3$): d 3.83 (s, 3H, OCH$_3$), 4.18 (s, 2H, SCH$_2$), 6.88 (m, 2H, Ar), 7.40 (m, 2H, Ar), 7.52 (m, 2H, Ar), 7.62 (m, 1H, Ar), 7.98 (m, 2H, Ar); CNMR (100 MHz, CDCl$_3$): δ 42.8, 55.4, 114.8, 124.6, 128.7, 128.8, 133.3, 134.7, 135.6, 159.8, 194.4; GC-MS m/z 258.1 (M$^+$).

1-(2,4-Difluoro-phenyl)-2-(4-methoxy-phenylsulfanyl)-ethanone (9m)

Purified by silica gel/hexane:ethyl acetate (4:1) column chromatography as a slightly yellow oil; yield 72% (2.12 g); H NMR (400 MHz, CDCl$_3$): d 3.83 (s, 3H, OCH$_3$), 4.13 (s, 2H, SCH$_2$), 6.85-6.95 (m, 3H, Ar), 7.02 (m, 1H, Ar), 7.33 (m, 2H, Ar), 7.92 (m, 1H, Ar); CNMR (100 MHz, CDCl$_3$): δ 46.8, 55.3, 104.7, 112.3, 114.7, 120.8, 124.1, 132.7, 133.3, 134.6, 159.8, 163.6, 164.7, 167.3, 190.9; IR ν (cm$^{-1}$) 3074, 3006, 2943, 1678, 1607, 1591, 1492, 1426, 1264, 1244, 1177, 1142, 1094, 1026, 968, 853, 824; GC-MS m/z 294.1 (M$^+$); ESI HRMS m/z calcd for C$_{15}$H$_{13}$F$_2$O$_3$S (M+OH)$^+$ 311.05480, found 311.05469.

1-(2,4-Difluoro-phenyl)-2-(3-hydroxy-phenylsulfanyl)-ethanone (9n)

Purified by silica gel/hexane:ethyl acetate (2:1) column chromatography as a yellow solid; mp 112-113° C.; yield 81% (2.27 g); H NMR (400 MHz, CDCl$_3$): d 4.28 (s, 2H, SCH$_3$), 5.28 (s, 1H, OH), 6.75 (m, 1H, Ar), 6.89-7.05 (m, 4H, Ar), 7.18 (m, 1H, Ar), 7.97 (m, 1H, Ar); CNMR (100 MHz, CDCl$_3$): δ 44.8, 104.8, 112.5, 114.3, 116.8 120.6, 122.4, 130.1, 133.3, 135.9, 156.0, 161.1, 163.8, 165.0, 167.6, 191.1; IR ν (cm$^{-1}$) 3457, 3048, 3008, 2988, 1668, 1609, 1586, 1492, 1430, 1389, 1304, 1263, 1222, 1093, 995, 964, 889, 848, 759; GC-MS m/z 280.1 (M$^+$); ESI HRMS m/z calcd for C$_{14}$H$_{11}$F$_2$O$_2$S (M+H)$^+$ 281.04423, found 281.04417.

1-(2,4-Difluoro-phenyl)-2-(3-triisopropylsilanyloxyphenylsulfanyl)-ethanone (9n')

To a 100 mL three-neck round bottom flask was added 9n (1.4 g, 5 mmol) and TIPSCl (1.15 g, 6 mmol) in CH$_2$Cl$_2$ (40 mL) under nitrogen at room temperature. Then a solution of imidazole (816 mg, 12 mmol) in CH$_2$Cl$_2$ (20 mL) was added dropwise. The resulting mixture was stirred for 24 h. The mixture was filtered and the solvents were removed under reduced pressure. The residue was purified by flash column chromatography eluted by hexane:ethyl acetate (6:1) and the correct product was obtained as a slightly yellow oil; yield 96% (2.1 g); H NMR (400 MHz, CDCl$_3$): d 1.13 (m, 18H, 6×CH$_3$), 1.29 (m, 3H, CH), 4.26 (s, 2H, SCH$_2$), 6.75 (m, 1H, Ar), 6.89-6.97 (m, 4H, Ar), 7.15 (m, 1H, Ar), 7.95 (m, 1H, Ar); CNMR (100 MHz, CDCl$_3$): δ 21.6, 17.7, 29.3, 104.3, 111.5, 118.5, 119.2, 121.5, 122.7, 129.5, 131.4, 135.9, 153.6, 156.3, 159.5, 162.3, 164.9; IR ν (cm$^{-1}$) 2944, 2983, 2866, 1682, 1610, 1584, 1475, 1423, 1266, 1245, 1186, 1145, 1095, 997, 970, 943, 881, 852, 776, 683; ESI HRMS m/z calcd for C$_{23}$H$_{31}$F$_2$O$_3$SSi (M+OH)$^+$ 453.17258, found 453.17226.

1-Phenyl-2-(pyridine-3-yloxy)-ethanone (9o)

To a suspension NaH (0.8 g, 60%, 20 mmol) in DMF (15 mL) was added a solution of 3-hydroxylpyridine (1.9 g, 20 mmol) in DMF (10 mL) at ° C. under nitrogen. After the mixture was stirred 15 min, a solution of 2-bromoacetophenone (3.98 g, 20 mmol) in DMF (10 mL) was added dropwise. The resulting mixture was stirred for 5 h until the starting material consumed. Water was added to quench the reaction and the aqueous phase was extracted with CH$_2$Cl$_2$ (3×40 mL). The combined organic phases were washed with brine, dried over MgSO$_4$ and concentrated under reduced pressure. The residue was purified by flash column chromatography eluted by hexane:ethyl acetate (1:1) and the correct product was obtained as a white solid; mp 81-82° C.; yield 75% (3.19 g); H NMR (400 MHz, CDCl$_3$): d 5.40 (s, 2H, OCH$_2$), 7.28 (m, 2H, Ar), 7.59 (m, 2H, Ar), 7.67 (m, 1H, Ar), 8.03 (m, 2H, Ar), 8.32 (m, 1H, Ar), 8.43 (m, 1H, Ar); CNMR (100 MHz, CDCl$_3$): δ 70.8, 121.7, 123.9, 128.1, 129.0, 134.2, 134.3, 138.2, 143.1, 154.4, 193.6; IR ν (cm$^{-1}$) 3054, 3007, 2988, 2963, 2898, 1702, 1579, 1486, 1450, 1422, 1275, 1263, 1233, 1090, 974, 815, 765, 751.

2-(6-Chloro-pyridin-2-yloxy)-1-phenyl-ethanone (9p)

Purified by silica gel/hexane:ethyl acetate (5:1) column chromatography as a yellow solid; mp 56-57° C. yield 82% (4.02 g); H NMR (400 MHz, CDCl$_2$): d 5.69 (s, 2H, OCH$_3$), 6.91-6.99 (m, 2H, Ar), 7.54-7.69 (m, 4H, Ar), 8.03 (m, 2H, Ar); CNMR (100 MHz, CDCl$_3$): δ 67.9, 109.4, 117.2, 127.9, 128.9, 133.7, 134.8, 141.1, 148.1, 162.3, 193.8; IR ν (cm$^{-1}$) 2935, 2857, 1703, 1586, 1562, 1450, 1401, 1367, 1301, 1257, 1222, 1160, 1137, 1085, 972, 874, 787, 749, 681; ESI HRMS m/z calcd for C$_{13}$H$_{11}$ClNO$_2$ (M+H)$^+$ 248.04728, found 248.04710.

2. General Procedure for the Preparation of Oximes

A 100 mL round bottom flask was charged with magnetic stirrer, corresponding ketone (5 mmol), NH$_2$OH.HCl (12.5 mmol), pyridine (2 mL) and EtOH (30 mL). The resulting mixture was stirred in an ice-bath overnight. The solvents were evaporated under reduced pressure and the residue treated with 1 N aqueous HCl (40 mL). The aqueous phase was extracted with ether (3×30 mL) and the combined organic phases were dried over anhydrous MgSO$_4$. The solvents were removed under vacuum and the residue was recrystallized or purified by flash column chromatography.

(Z)-2-(2,6-Dimethyl-phenoxy)-1-phenyl-ethanone oxime (10a)

Purified by recrystallization in hexane and ethyl acetate; yield 71% (1.8 g); mp 126-127° C., lit. 131-132° C.; H NMR (400 MHz, CDCl$_3$): d 2.34 (s, 6H, CH$_3$), 5.12 (s, 2H, OCH$_2$), 6.97 (m, 1H, Ar), 7.05 (m, 2H, Ar), 7.49 (m, 3H, Ar), 7.83 (m, 2H, Ar), 8.94 (br, 1H, OH); CNMR (100 MHz, CDCl$_3$): δ 16.5, 63.9, 124.2, 127.3, 128.5, 128.9, 129.5, 131.0, 134.2, 156.1, 156.4.

(E)-1-(2,6-Dimethyl-phenoxy)-propan-2-one oxime (10b)

Purified by recrystallization in hexane; yield 57% (4.5 g); mp 70-71° C.; H NMR (400 MHz, CDCl$_3$): d 2.19 (s, 3H, CH$_3$), 2.35 (s, 6H, CH$_3$), 4.37 (s, 2H, OCH$_2$), 7.01 (m, 1H, Ar), 7.07 (m, 2H, Ar), 7.88 (br, 1H, OH); CNMR (100 MHz, CDCl$_3$): δ 11.8, 16.4, 73.2, 124.3, 129.0, 130.9, 155.4, 155.5; GC-MS m/z 193.1 (M$^+$).

Z)-2-(2,6-Dimethyl-phenoxy)-1-(4-fluoro-phenyl)-ethanone oxime (10c)

Purified by recrystallization in hexane and ethyl acetate; yield 61% (1.4 g); mp 82-83° C.; H NMR (400 MHz, CDCl$_3$): d 2.32 (s, 6H, CH$_3$), 5.08 (s, 2H, OCH$_2$), 6.99 (m, 1H, Ar), 7.07 (m, 2H, Ar), 7.16 (m, 2H, Ar), 7.82 (m, 2H, Ar), 7.98 (br, 1H, OH); CNMR (100 MHz, CDCl$_3$): δ 16.5, 63.8, 115.4, 124.3, 129.2, 130.3, 130.9, 155.6, 156.0, 162.4, 164.9; IR ν

(cm⁻¹) 3175, 3024, 2884, 1602, 1511, 1462, 1441, 1318, 1262, 1238, 1191, 1079, 1055, 985, 956, 840, 767; GC-MS m/z 273.1 (M⁺); ESI HRMS m/z calcd for $C_{16}H_{17}FNO_2$ (M+H)⁺ 274.12378, found 274.12357.

(Z)-1-(4-Fluoro-phenyl-2-o-tolyloxy-ethane oxime (10d)

Purified by recrystallization in hexane and ethyl acetate; yield 67% (1.41 g); mp 107-108° C.; H NMR (400 MHz, CDCl₃): d 2.11 (s, 3H, CH₃), 5.34 (s, 2H, OCH₂), 6.91-6.99 (m, 2H, Ar), 7.08-7.23 (m, 4H, Ar), 7.71 (m, 2H, Ar); 8.34 (s, 1H, OH); CNMR (100 MHz, CDCl₃): δ 16.2, 59.8, 110.9, 115.2, 121.1, 126.8, 127.0, 129.5, 130.8, 155.9, 156.0, 161.0, 164.9; IR ν (cm⁻¹) 3032, 2948, 2869, 1601, 1508, 1490, 1459, 1453, 1310, 1257, 1221, 1191, 1158, 1124, 1029, 995, 930, 842, 747; GC-MS m/z 259.1 (M⁺); ESI HRMS m/z calcd for $C_{15}H_{15}FNO_2$ (M+H)⁺ 260.10813, found 260.10794.

(Z)-1-(4-Chloro-phenyl)-2-o-tolyloxy-ethanone oxime (10e)

Purified by recrystallization in hexane and ethyl acetate; yield 65% (1.47 g); mp 115-116° C.; H NMR (400 MHz, CDCl₃): d 2.12 (s, 3H, CH₃), 5.34 (s, 2H, OCH₂), 6.91-6.99 (m, 2H, Ar), 7.14-7.23 (m, 2H, Ar), 7.39 (m, 2H, Ar); 7.66 (m, 2H, Ar), 8.22 (s, 1H, OH); CNMR (100 MHz, CDCl₃): δ 16.2, 59.6, 110.9, 121.2, 126.9, 127.0, 128.5, 128.6, 130.9, 131.9, 135.6, 155.7, 156.0; IR ν (cm⁻¹) 3218, 3083, 1589, 1492, 1461, 1441, 1362, 1324, 1236, 1191, 1126, 1094, 1069, 1014, 952, 944, 827, 747; GC-MS m/z 275.0 (M⁺); ESI HRMS m/z calcd for $C_{15}H_{15}ClNO_2$ (M+H)⁺ 276.07858, found 276.07840.

(Z)-1-(4-Chloro-phenyl)-2-(2,6-dimethyl-phenoxy)-ethanone oxime (10f)

Purified by recrystallization in hexane and ethyl acetate; yield 59% (1.65 g); mp 88-90° C.; H NMR (400 MHz, CDCl₃): d 2.33 (s, 6H, CH₃), 5.07 (s, 2H, OCH₂), 7.01 (m, 1H, Ar), 7.05 (m, 2H, Ar), 7.45 (m, 2H, Ar), 7.78 (m, 2H, Ar), 7.8 (s, 1H, OH); CNMR (100 MHz, CDCl₃): δ 16.5, 63.6, 124.3, 128.6, 128.7, 129.0, 130.9, 132.7, 135.6, 155.6, 156.0; 156.0; IR ν (cm⁻¹) 3167, 3040, 1596, 1494, 1474, 1318, 1261, 1190, 1093, 1049, 988, 959, 836, 815, 797, 761; ESI HRMS m/z calcd for $C_{16}H_{17}ClNO_2$ (M+H)⁺ 290.09423, found 290.09402.

(Z)-2-(2-Chloro-phenoxy)-1-(4-chloro-phenyl)-ethanone oxime (10 g)

Purified by recrystallization in hexane and ethyl acetate; yield 81% (1.8 g); mp 129-130° C.; H NMR (400 MHz, CDCl₃): d 5.41 (s, 2H, OCH₂), 6.93 (m, 1H, Ar), 7.06 (m, 1H, Ar), 7.23 (m, 1H, Ar), 7.37 (m, 3H, Ar), 7.78 (m, 2H, Ar), 8.35 (s, 1H, OH); CNMR (100 MHz, CDCl₃): δ 60.7, 113.6, 122.3, 123.2, 127.7, 128.6, 128.7, 130.5, 131.4, 135.8, 153.3, 155.0; IR ν (cm⁻¹) 3242, 3071, 1697, 1588, 1570, 1484, 1467, 1443, 1272, 1221, 1083, 1062, 1009, 969, 933, 850, 825, 737; ESI HRMS m/z calcd for $C_{14}H_{12}Cl_2NO_2$ (M+H)⁺ 296.02395, found 296.02377.

(Z)-1-Phenyl-2-o-tolyloxy-ethanone oxime (10h)

Purified by recrystallization in hexane and ethyl acetate; yield 76% (2.1 g); mp 106-107° C.; H NMR (400 MHz, CDCl₃): d 2.11 (s, 3H, CH₃), 5.37 (s, 2H, OCH₂), 6.91 (m, 1H, Ar), 7.00 (m, 1H, Ar), 7.15 (m, 1H, Ar), 7.23 (m, 1H, Ar), 7.41 (m, 3H, Ar), 7.72 (m, 2H, Ar), 8.81 (s, 1H, OH); CNMR (100 MHz, CDCl₃): δ 16.2, 60.0, 111.0, 121.0, 126.8, 127.1, 127.3, 128.3, 129.5, 130.8, 133.5, 156.2, 156.6; IR ν (cm⁻¹) 3202, 3020, 2910, 1590, 1493, 1458, 1308, 1274, 1261, 1221, 1186, 1121, 1045, 996, 940, 912, 749; GC-MS m/z 241.2 (M⁺).

(Z)-2-(4-Chloro-phenoxy)-1-phenyl-ethanone oxime (10i)

Purified by recrystallization in hexane and ethyl acetate; yield 75% (1.9 g); mp 122-123° C.; H NMR (400 MHz, CDCl₃): d 5.32 (s, 2H, OCH₂), 6.91 (m, 2H, Ar), 7.26 (m, 2H, Ar), 7.45 (m, 3H, Ar), 7.69 (m, 2H, Ar), 8.81 (br, 1H, OH); CNMR (100 MHz, CDCl₃): δ 60.0, 116.0, 126.4, 127.1, 128.5, 129.4, 129.7, 133.2, 155.8, 156.6; IR ν (cm⁻¹) 3206, 3063, 2927, 1586, 1481, 1471, 1314, 1276, 1225, 1171, 1091, 1008, 929, 812, 749.

(Z)-1-(2,3-Dihydro-benzo-[1,4]-dioxin-6-yl)-2-phenoxy-ethanone oxime (10j)

Purified by recrystallization in hexane and ethyl acetate; yield 67% (1.32 g); mp 104-106° C.; H NMR (400 MHz, CDCl₃): d 4.31 (m, 4H, OCH₂), 5.28 (s, 2H, OCH₂), 6.91 (m, 1H, Ar), 7.01 (m, 3H, Ar), 7.24 (m, 1H, Ar), 7.34 (m, 3H, Ar), 8.83 (br, 1H, OH); CNMR (100 MHz, CDCl₃): δ 59.6, 64.3, 64.5, 114.7, 116.2, 117.2, 120.6, 121.3, 126.9, 129.5, 143.4, 145.0, 155.2, 158.2.

(Z)-1-(2,3-Dihydro-benzo-[1,4]-dioxin-6-yl-2-o-tolyloxy-ethanone oxime (10k)

Purified by recrystallization in hexane and ethyl acetate; yield 60% (1.45 g); mp 115-116° C.; H NMR (400 MHz, CDCl₃): d 2.17 (s, 3H, CH₃), 4.31 (m, 4H, OCH₂), 5.28 (s, 2H, OCH₂), 6.90 (m, 2H, Ar), 7.01 (m, 1H, Ar), 7.14-7.25 (m, 3H, Ar), 7.31 (m, 1H, Ar), 8.61 (s, 1H, OH); CNMR (100 MHz, CDCl₃): δ 16.3, 59.7, 64.3, 64.5, 111.1, 116.3, 117.1, 120.7, 121.0, 126.8, 126.9, 127.1, 130.7, 143.3, 144.9, 155.6, 156.3; IR ν (cm⁻¹) 3237, 3066, 3007, 2947, 1579, 1510, 1494, 1458, 1326, 1313, 1279, 1253, 1225, 1190, 1124, 1068, 1052, 999, 891, 808, 753; ESI HRMS m/z calcd for $C_{17}H_{18}NO_4$ (M+H)⁺ 300.12303, found 300.12277.

(Z)-2-(4-Methoxy-phenylsulfanyl)-1-phenyl-ethanone oxime (10l)

Purified by recrystallization in hexane and ethyl acetate; yield 82% (1.31 g); mp 61-62° C.; H NMR (400 MHz, CDCl₃): d 3.83 (s, 3H, OCH₃), 4.17 (s, 2H, SCH₂), 6.83 (m, 2H, Ar), 7.40-7.45 (m, 5H, Ar), 7.63 (m, 2H, Ar), 8.10 (br, 1H, OH); CNMR (100 MHz, CDCl₃): δ 29.9, 55.3, 114.5, 125.4, 126.5, 128.5, 129.5, 134.6, 135.1, 155.6, 159.7; GC-MS m/z 273.1 (M⁺).

(Z)-1-(2,4-Difluoro-phenyl)-2-(4-methoxy-phenylsulfanyl)-ethanone oxime (10m)

Purified by silica gel/hexane:ethyl acetate (8:1-4:1) column chromatography as white solid; yield 78% (1.23 g); mp 98-99° C.; H NMR (400 MHz, CDCl₃): d 3.83 (s, 3H, OCH₃), 4.19 (m, 2H, SCH₂), 6.80-6.93 (m, 4H, Ar), 7.29-7.38 (m, 3H, Ar), 8.23 (s, 1H, OH); CNMR (100 MHz, CDCl₃): δ 31.0, 55.3, 104.3, 111.5, 114.4, 119.5, 124.9, 131.4, 134.3, 153.7, 159.5, 162.3, 164.8; IR ν (cm⁻¹) 3202, 3075, 3008, 1587, 1491, 1409, 1316, 1277, 1265, 1243, 1171, 1140, 1098, 1063, 1025, 972, 932, 819, 764; ESI HRMS m/z calcd for $C_{15}H_{14}F_2NO_2S$ (M+H)$^+$ 4 310.07077, found 310.07050.

(Z)-1-(2,4-Difluoro-phenyl)-2-(3-TIPS-phenylsulfanyl)-ethanone oxime (10n)

Purified by silica gel/hexane:ethyl acetate (15:1-10:1) column chromatography as white solid; yield 71% (1.6 g); mp 54-56° C.; H NMR (400 MHz, CDCl$_3$): d 1.12 (m, 18H, CH$_3$), 1.27 (m, 3H, CH), 4.28 (s, 2H, SCH$_2$), 6.73 (m, 1H, Ar), 6.85-6.90 (m, 4H, Ar), 7.09 (m, 1H, Ar), 7.32 (m, 1H, Ar), 8.72 (br, 1H, OH); CNMR (100 MHz, CDCl$_3$): δ 12.6, 17.9, 29.3, 104.1, 111.5, 118.5, 119.2, 121.5, 122.7, 129.5, 131.4, 135.9, 153.6, 156.3, 159.5, 161.8, 165.0; IR ν (cm$^{-1}$) 3256, 3071, 2955, 2868, 1617, 1583, 1508, 1475, 1420, 1315, 1269, 1248, 1141, 1098, 1063, 998, 970, 953, 932, 880, 859; ESI HRMS m/z calcd for $C_{23}H_{32}F_2NO_2SSi$ (M+H)$^+$ 452.18855, found 452.18817.

(Z)-1-Phenyl-2-(pyridine-3-yloxy)-ethanone oxime (10o)

Purified by recrystallization in ethyl acetate and ethanol; yield 60% (1.8 g); mp 138-140° C.; H NMR (400 MHz, DMSO): d 5.34 (s, 2H, OCH$_2$), 7.32-7.42 (m, 5H, Ar), 7.66 (m, 2H, Py), 8.17 (m, 1H, Py), 8.26 (m, 1H, Py), 12.0 (s, 1H, OH); CNMR (100 MHz, DMSO): δ 59.4, 121.5, 124.6, 126.8, 128.8, 129.5, 134.6, 138.2, 142.7, 152.9, 154.6; IR ν (cm$^{-1}$) 2964, 2576, 1591, 1492, 1427, 1279, 1225, 1192, 1104, 1080, 1015, 992, 945, 800, 767, 753, 699; ESI HRMS m/z calcd for $C_{13}H_{13}N_2O_2$ (M+H)$^+$ 229.09715, found 229.09695.

(Z)-2-(6-Chloro-pyridin-2-yloxy)-1-phenyl-ethanone oxime (10p)

Purified by silica gel/hexane:ethyl acetate (6:1-4:1) column chromatography as white solid; yield 68% (2.8 g); mp 100-102° C.; H NMR (400 MHz, CDCl$_3$): d 5.60 (s, 2H, OCH$_2$), 6.69 (d, 1H, J=8.4 Hz, Ar), 6.97 (d, 1H, J=7.2 Hz, Ar), 7.43 (m, 3H, Ar), 7.54 (m, 1H, Ar), 7.70 (m, 2H, Ar), 8.92 (s, 1H, OH); CNMR (100 MHz, DMSO): δ 58.3, 109.3, 117.0, 127.0, 128.5, 129.5, 133.8, 140.8, 148.3, 155.6, 162.6; IR ν (cm$^{-1}$) 3282, 1598, 1563, 1500, 1442, 1405, 1372, 1308, 1254, 1167, 1081, 1001, 942, 926, 795, 762; ESI HRMS m/z calcd for $C_{13}H_{12}ClN_2O_2$ (M+H)$^+$ 263.05818, found 263.04713.

3. General Procedure for the Preparation of O-benzyl Oximes

To a suspension of NaH (1.1 equiv) in DMF was added dropwise a solution of hydroxyl oxime (1.0 equiv) maintaining the temperature at −30° C. After the addition, the reaction mixture was stirred for 1 h. Then, BnBr (1.05 equiv) in DMF was added dropwise at the same temperature. The resulting mixture was stirred overnight, allowed to warm to room temperature, and then quenched with saturated aqueous NH$_4$Cl solution and extracted with ether. The combined organic phases were washed with brine, dried over anhydrous MgSO$_4$ and concentrated under reduced pressure. The residue was purified by flash silica gel column chromatography.

(Z)-2-(2,6-Dimethyl-phenoxy)-1-phenyl-ethanone O-benzyl oxime (11a)

Purified by silica gel/hexane:ethyl acetate (15:1) column chromatography as a white solid; mp 41-42° C.; yield 91% (6.5 g); H NMR (400 MHz, CDCl$_3$): d 2.28 (s, 6H, CH$_3$), 5.06 (s, 2H, OCH$_2$), 5.29 (s, 2H, OCH$_2$), 6.98-7.05 (m, 3H, Ar), 7.38-7.41 (m, 5H, Ar), 7.45-7.47 (m, 3H, Ar), 7.86 (m, 2H, Ar); CNMR (100 MHz, CDCl$_3$): δ 16.5, 64.3, 76.7, 124.1, 127.3, 127.9, 128.4, 128.9, 129.3, 131.0, 134.4, 137.4, 155.3, 156.1; IR ν (cm$^{-1}$) 3087, 3028, 2913, 2865, 1495, 1473, 1443, 1371, 1328, 1305, 1262, 1196, 1092, 1043, 1025, 987, 944, 915, 845, 764, 729, 688; GC-MS m/z 345.1 (M$^+$); ESI HRMS m/z calcd for $C_{23}H_{24}NO_2$ (M+H)$^+$ 346.18015, found 346.17979.

(E)-1-(2,6-Dimethyl-phenoxy)-propan-2-one O-benzyl oxime (11b)

Purified by silica gel/hexane:ethyl acetate (15:1) column chromatography as a colorless oil; yield 84% (2.32 g); H NMR (400 MHz, CDCl$_3$): d 2.20 (s, 3H, CH$_3$), 2.34 (s, 6H, CH$_3$), 4.37 (s, 2H, OCH$_2$), 5.21 (s, 2H, OCH$_2$), 6.99 (m, 1H, Ar), 7.07 (m, 2H, Ar), 7.37-7.43 (m, 5H, Ar); CNMR (100 MHz, CDCl$_3$): δ 12.8, 16.5, 73.4, 75.9, 124.2, 127.8, 128.0, 128.4, 128.9, 131.0, 138.0, 154.7, 155.6; GC-MS m/z 283.1 (M$^+$).

(Z)-2-(2,6-Dimethyl-phenoxy)-1-(4-fluoro-phenyl)-ethanone O-benzyl oxime (11c)

Purified by silica gel/hexane:ethyl acetate (15:1) column chromatography as a colorless oil; yield 96% (2.38 g); H NMR (400 MHz, CDCl$_3$): d 2.29 (s, 6H, CH$_3$), 5.05 (s, 2H, OCH$_2$), 5.28 (s, 2H, OCH$_2$), 6.99-7.06 (m, 3H, Ar), 7.17 (m, 2H, Ar), 7.41 (m, 5H, Ar), 7.87 (m, 2H, Ar); CNMR (100 MHz, CDCl$_3$): δ 16.5, 64.3, 76.7, 115.3, 124.2, 128.0, 128.4, 129.2, 130.4, 130.5, 130.9, 137.3, 154.4, 156.1, 162.3, 164.8; IR ν (cm$^{-1}$) 3064, 3032, 2924, 2861, 1603, 1510, 1474, 1453, 1365, 1326, 1263, 1231, 1189, 1159, 1093, 1003, 981, 927, 885, 832, 766, 696; ESI HRMS m/z calcd for $C_{23}H_{23}FNO_2$ (M+H)$^+$ 364.17073, found 364.17028.

(Z)-1-(4-Fluoro-phenyl)-2-o-tolyloxy-ethanone O-benzyl oxime (11d)

Purified by silica gel/hexane:ethyl acetate (15:1) column chromatography as a white solid; mp 64-65° C.; yield 84% (1.23 g); H NMR (400 MHz, CDCl$_3$): d 2.09 (s, 3H, CH$_3$), 5.30 (s, 2H, OCH$_2$), 5.34 (s, 2H, OCH$_2$), 6.87 (m, 2H, Ar), 7.04-7.13 (m, 4H, Ar), 7.41-7.50 (m, 5H, Ar), 7.70 (m, 2H, Ar); CNMR (100 MHz, CDCl$_3$): δ 16.2, 60.4, 76.7, 111.0, 115.0, 121.0, 126.7, 128.1, 128.5, 129.3, 129.7, 130.8, 137.5, 154.6, 156.0; IR ν (cm$^{-1}$) 3032, 2948, 2869, 1601, 1508, 1490, 1460, 1451, 1308, 1259, 1221, 1189, 1158, 1124, 1029, 929, 843, 747, 694; GC-MS m/z 349.1 (M$^+$); ESI HRMS m/z calcd for $C_{22}H_{21}FNO_2$ (M+H)$^+$ 350.15537, found 350.15469.

(Z)-1-(4-Chloro-phenyl)-2-o-tolyloxy-ethanone O-benzyl oxime (11e)

Purified by silica gel/hexane:ethyl acetate (15:1) column chromatography as a white solid; mp 107-108° C.; yield 84% (1.62 g); H NMR (400 MHz, CDCl$_3$): d 2.11 (s, 3H, CH$_3$), 5.30 (s, 2H, OCH$_2$), 5.36 (s, 2H, OCH$_2$), 6.87 (m, 2H, Ar), 7.17 (m, 2H, Ar), 7.36-7.51 (m, 7H, Ar), 7.69 (m, 2H, Ar); CNMR (100 MHz, CDCl$_3$): δ 16.2, 60.2, 76.7, 111.0, 121.0, 126.8, 126.9, 128.2, 128.4, 128.45, 128.5, 128.6, 130.8, 132.1, 135.3, 137.4, 154.4, 156.0; IR ν (cm$^{-1}$) 3028, 2945, 2873, 1589, 1490, 1461, 1453, 1310, 1258, 1221, 1191, 1124, 1094, 1015, 1028, 932, 819, 747, 697; ESI HRMS m/z calcd for $C_{22}H_{21}ClNO_2$ (M+H)$^+$ 366.12553, found 366.12515.

(Z)-1-(4-Chloro-phenyl)-2-(2,6-dimethyl-phenoxy)-ethanone O-benzyl oxime (11f)

Purified by silica gel/hexane:ethyl acetate (15:1) column chromatography as a white solid; mp 56-57° C.; yield 88% (0.695 g); H NMR (400 MHz, CDCl$_3$): d 2.27 (s, 6H, CH$_3$), 5.04 (s, 2H, OCH$_2$), 5.23 (s, 2H, OCH$_2$), 6.98-7.05 (m, 3H, Ar), 7.37-7.45 (m, 7H, Ar), 7.81 (m, 2H, Ar); CNMR (100 MHz, CDCl$_3$): δ 16.5, 64.2, 76.7, 124.2, 128.0, 128.4, 128.58, 128.63, 128.9, 130.9, 132.8, 135.4, 137.2, 154.3, 156.0; IR ν (cm$^{-1}$) 3032, 2948, 2885, 1473, 1368, 1262, 1189, 1180, 1094, 1023, 992, 934, 852, 817, 763, 741, 694; ESI HRMS m/z calcd for $C_{23}H_{23}ClNO_2$ (M+H)$^+$ 380.14118, found 380.14074.

(Z)-2-(2-Chloro-phenoxy)-1-(4-chloro-phenyl)-ethanone O-benzyl oxime (11g)

Purified by silica gel/hexane:ethyl acetate (15:1) column chromatography as a white solid; mp 96-97° C.; yield 89% (1.85 g); H NMR (400 MHz, CDCl$_3$): 5.34 (s, 2H, OCH$_2$), 5.36 (s, 2H, OCH$_2$), 6.93 (m, 2H, Ar), 7.12 (m, 1H, Ar), 7.32-7.47 (m, 8H, Ar), 7.71 (m, 2H, Ar); CNMR (100 MHz, CDCl$_3$): δ 61.1, 76.7, 113.6, 122.1, 123.1, 127.6, 128.2, 128.5, 128.55, 128.57, 128.7, 130.4, 131.5, 135.5, 137.2, 153.3, 153.6; IR ν (cm$^{-1}$) 3067, 3040, 2964, 2878, 1586, 1479, 1454, 1373, 1279, 1253, 1228, 1094, 1068, 1027, 993, 929, 826, 799, 739, 670; ESI HRMS m/z calcd for $C_{21}H_{18}Cl_2NO_2$ (M+H)$^+$ 386.0709, found 386.07051.

(Z)-1-Phenyl-2-o-tolyloxy-ethanone O-benzyl oxime (11h)

Purified by silica gel/hexane:ethyl acetate (15:1) column chromatography as a white solid; mp 50-51° C.; yield 90% (2.08 g); H NMR (400 MHz, CDCl$_3$): d 2.11 (s, 3H, CH$_3$), 5.33 (s, 2H, OCH$_2$), 5.38 (s, 2H, OCH$_2$), 6.91 (m, 2H, Ar), 7.16 (m, 2H, Ar), 7.41-7.53 (m, 8H, Ar), 7.78 (m, 2H, Ar); CNMR (100 MHz, CDCl$_3$): δ 16.2, 60.4, 76.7, 111.1, 120.9, 126.8, 127.0, 127.3, 128.0, 128.2, 128.4, 128.5, 129.3, 130.7, 133.7, 137.6, 155.4, 156.2; IR ν (cm$^{-1}$) 3060, 3033, 2944, 2908, 2867, 1601, 1590, 1494, 1461, 1372, 1307, 1275, 1257, 1219, 1187, 1123, 1025, 932, 912, 754, 691; ESI HRMS m/z calcd for $C_{22}H_{22}NO_2$ (M+H)$^+$ 332.1645, found 332.16409.

(Z)-2-(4-Chloro-phenoxy)-1-phenyl-ethanone O-benzyl oxime

Purified by silica gel/hexane:ethyl acetate (15:1) column chromatography as a white solid; mp 48-49° C.; yield 85% (1.69 g); H NMR (400 MHz, CDCl$_3$): 5.28 (s, 2H, OCH$_2$), 5.36 (s, 2H, OCH$_2$), 6.82 (m, 2H, Ar), 7.18 (m, 2H, Ar), 7.39-7.49 (m, 8H, Ar), 7.72 (m, 2H, Ar); CNMR (100 MHz, CDCl$_3$): δ 60.6, 76.7, 116.1, 126.2, 127.1, 128.2, 128.3, 128.6, 129.3, 129.5, 133.4, 137.4, 154.6, 156.6; IR ν (cm$^{-1}$) 3060, 3031, 2933, 2873, 1595, 1583, 1489, 1455, 1284, 1233, 1213, 1171, 1093, 1006, 929, 882, 822, 759, 748, 692; ESI HRMS m/z calcd for $C_{21}H_{19}ClNO_2$ (M+H)$^+$ 352.10988, found 352.10953.

(Z)-1-(2,3-Dihydro-benzo[1,4]dioxin-6-yl)-2-phenoxy-ethanone O-benzyl oxime (11j)

Purified by silica gel/hexane:ethyl acetate (5:1) column chromatography as a white solid; mp 84-85° C.; yield 83% (1.15 g); H NMR (400 MHz, CDCl$_3$): 4.28-4.32 (m, 4H, OCH$_2$), 5.23 (s, 2H, OCH$_2$), 5.32 (s, 2H, OCH$_2$), 6.86-7.00 (m, 4H, Ar), 7.23-7.28 (m, 4H, Ar), 7.30-7.37 (m, 5H, Ar); CNMR (100 MHz, CDCl$_3$): δ 60.2, 64.3, 64.5, 76.7, 114.8, 116.2, 117.1, 120.7, 121.2, 127.1, 128.0, 128.45, 128.47, 129.4, 137.6, 143.3, 144.8, 154.1, 158.2; IR ν (cm$^{-1}$) 3063, 3007, 2989, 2926, 2853, 1596, 1505, 1488, 1455, 1425, 1326, 1276, 1262, 1217, 1175, 1065, 1049, 1000, 974, 885, 856, 813, 751, 730, 699; ESI HRMS m/z calcd for $C_{23}H_{22}NO_4$ (M+H)$^+$ 376.15406, found 376.15382.

(Z)-1-(2,3-Dihydro-benzo-[1,4]-dioxin-6-yl)-2-o-tolyloxy-ethanone O-benzyl oxime (11k)

Purified by silica gel/hexane:ethyl acetate (5:1) column chromatography as a oil; yield 96% (0.89 g); H NMR (400 MHz, CDCl$_3$): d 2.18 (s, 3H, CH$_3$), 4.28-4.32 (m, 4H, OCH$_2$), 5.27 (s, 2H, OCH$_2$), 5.35 (s, 2H, OCH$_2$), 6.90 (m, 3H, Ar), 7.11 (m, 2H, Ar), 7.26-7.35 (m, 2H, Ar), 7.41-7.47 (m, 5H, Ar); CNMR (100 MHz, CDCl$_3$): δ 16.3, 60.3, 64.3, 64.6, 76.7, 111.2, 116.3, 117.0, 120.8, 120.9, 126.8, 127.05, 127.1, 128.0, 128.4, 128.5, 130.7, 137.7, 143.3, 144.8, 154.5, 156.3; IR ν (cm$^{-1}$) 3063, 3028, 2977, 2931, 2878, 1603, 1590, 1574, 1508, 1494, 1455, 1427, 1329, 1309, 1283, 1240, 1188, 1122, 1066, 1013, 887, 812, 749, 697; ESI HRMS m/z calcd for $C_{24}H_{24}NO_4$ (M+H)$^+$ 390.16998, found 390.16952.

(Z)-2-(4-Methoxy-phenylsulfanyl)-1-phenyl-ethanone O-benzyl oxime (11l)

Purified by silica gel/hexane:ethyl acetate (10:1) column chromatography as a slightly yellow oil; yield 85% (1.03 g); H NMR (400 MHz, CDCl$_3$): d 3.83 (s, 3H, CH$_3$), 4.15 (s, 2H, SCH$_2$), 5.15 (s, 2H, OCH$_2$), 6.90 (m, 2H, Ar), 7.36-7.41 (m, 10H, Ar), 7.67 (m, 2H, Ar); CNMR (100 MHz, CDCl$_3$): δ 30.6, 55.3, 76.3, 114.4, 125.5, 126.5, 127.8, 128.2, 128.3, 128.4, 129.3, 134.7, 135.2, 137.6, 154.4, 159.6; IR ν (cm$^{-1}$) 3063, 3028, 2927, 1591, 1571, 1492, 1455, 1442, 1365, 1324, 1285, 1244, 1172, 1025, 981, 930, 881, 825, 747, 691; ESI HRMS m/z calcd for $C_{22}H_{22}NO_2S$ (M+H)$^+$ 364.13657, found 364.13621.

(Z)-1-(2,4-Difluoro-phenyl)-2-(4-methoxy-phenylsulfanyl)-ethanone O-benzyl oxime (11m)

Purified by silica gel/hexane:ethyl acetate (10:1) column chromatography as a slightly yellow oil; yield 89% (0.886 g); H NMR (400 MHz, CDCl$_3$): d 3.83 (s, 3H, CH$_3$), 4.20 (s, 2H, SCH$_2$), 5.16 (s, 2H, OCH$_2$), 6.75 (m, 2H, Ar), 6.81-6.92 (m, 2H, Ar), 7.27 (m, 2H, Ar), 7.32-7.48 (m, 6H, Ar); CNMR (100 MHz, CDCl$_3$): δ 31.8, 55.3, 76.5, 104.5, 111.6, 114.5, 119.5, 125.1, 128.2, 129.2, 131.7, 134.2, 134.7, 137.3, 152.8, 159.5, 162.2, 164.7; IR ν (cm$^{-1}$) 3066, 3032, 2938, 2837, 1607, 1591, 1493, 1456, 1418, 1365, 1326, 1285, 1267, 1244, 1175, 1139, 1099, 1026, 968, 925, 879, 850, 820, 731, 697; ESI HRMS m/z calcd for $C_{22}H_{20}F_2NO_2S$ (M+H)$^+$ 400.11773, found 400.11722.

(Z)-2-(3-Benzyloxy-phenylsulfanyl)-1-(2,4-difluoro-phenyl)-ethanone O-benzyl oxime (11n)

Purified by silica gel/hexane:ethyl acetate (10:1) column chromatography as a slightly yellow oil; yield 89% (0.886 g); H NMR (400 MHz, CDCl$_3$): d 4.30 (s, 2H, SCH$_3$), 5.03 (s, 2H, OCH$_2$), 5.24 (s, 2H, OCH$_2$), 6.83-6.90 (m, 4H, Ar), 6.95 (m, 1H, Ar), 7.15 (m, 1H, Ar), 7.30-7.46 (m, 11H, Ar); CNMR (100 MHz, CDCl$_3$): δ 30.1, 69.9, 76.7, 103.9, 111.1, 113.4, 116.3, 119.2, 122.6, 127.5, 128.0, 128.6, 129.6, 131.6, 136.7, 137.1, 152.7, 158.9, 159.3, 161.9, 162.4, 164.7, 164.9; IR ν (cm$^{-1}$) 3067, 3032, 2929, 2869, 1611, 1586, 1574, 1503, 1477, 1454, 1422, 1379, 1325, 1267, 1223, 1139, 1100, 1080, 1015, 967, 849, 817, 732, 696; ESI HRMS m/z calcd for $C_{28}H_{24}F_2NO_2S$ (M+H)$^+$ 476.14902, found 476.14828.

(Z)-1-Phenyl-2-(pyridine-3-yloxy)-ethanone O-benzyl oxime (11o)

Purified by silica gel/hexane:ethyl acetate (1:1) column chromatography as a colorless oil; yield 90% (1.15 g); H NMR (400 MHz, CDCl$_3$): d 5.35 (s, 2H, OCH$_2$), 5.37 (s, 2H, OCH$_2$), 7.13-7.21 (m, 2H, Ar), 7.40-7.52 (m, 8H, Ar), 7.32 (m, 2H, Ar), 8.24 (m, 1H, Ar), 8.33 (m, 1H, Ar); CNMR (100 MHz, CDCl$_3$): δ 60.4, 76.7, 121.1, 123.8, 127.1, 128.2, 128.4, 128.6, 129.6, 133.2, 137.3, 138.6, 142.7, 154.2, 154.3; IR ν (cm$^{-1}$) 3064, 3032, 2927, 2877, 1574, 1474, 1455, 1426, 1365, 1326, 1273, 1259, 1218, 1187, 1103, 1007, 929, 882, 798, 762, 747, 692; ESI HRMS m/z calcd for $C_{20}H_{19}N_2O_2$ (M+H)$^+$ 319.1441, found 319.14377.

(Z)-2-(6-Chloro-pyridin-2-yloxy)-1-phenyl-ethanone O-benzyl oxime (11p)

Purified by silica gel/hexane:ethyl acetate (8:1) column chromatography as a colorless oil; yield 87% (2.64 g); H NMR (400 MHz, CDCl$_3$): d 5.37 (s, 2H, OCH$_2$), 5.59 (s, 2H, OCH$_2$), 6.66 (d, 1H, J=8.4 Hz, Ar), 6.96 (d, 1H, J=7.6 Hz, Ar), 7.36-7.54 (m, 9H, Ar), 7.72 (m, 2H, Ar); CNMR (100 MHz, CDCl$_3$): δ 58.9, 76.8, 109.3, 116.9, 127.1, 127.9, 128.2, 128.3, 128.4, 129.3, 133.9, 137.7, 140.7, 148.3, 154.6, 162.7; IR ν (cm$^{-1}$) 3064, 3031, 2924, 2877, 1591, 1560, 1496, 1435, 1407, 1365, 1294, 1262, 1161, 1074, 1005, 985, 908, 882, 787, 763, 694; 692; ESI HRMS m/z calcd for $C_{20}H_{18}ClN_2O_2$ (M+H)$^+$ 353.10512, found 353.10486.

4. General Procedure for the Asymmetric Reduction of O-benzyl Oximes

To a 50 ml reaction tube with catalyst 6 (33 mg, 0.1 mmol) under N$_2$ was added 10 mL of anhydrous dioxane and 4 mL BH3.THF (1 M in THF) in one portion. In the case of pyridylethers, 5 mL BH3.THF (1 M in THF) was added. After stirring the mixture for 1 h at room temperature, the clear solution was cooled at 0° C. and the benzyl oxime (1 mmol) in 5 ml of dioxane was added drop-wise during 1 h using a syringe pump. The resulting mixture was stirred at 0° C. until the conversion was complete in about 48 h. Then, the reaction was quenched with 6N HCl and then 6N NaOH until the solution was basic. It was extracted with ether and the combined organic phases were washed with brine, dried over anhydrous MgSO$_4$ and concentrated under reduced pressure. The residue was purified by flash column chromatography and the correct product was obtained.

(R)-2-(2,6-Dimethyl-phenoxy)-1-phenyl-ethylamine (12a)

Purified by silica gel/hexane:ethyl acetate (2:1) column chromatography as a colorless oil; yield 84% (101 mg); 97% ee; $[α]^{20}_D$=−28.5 (c 1.2, CHCl$_3$); H NMR (400 MHz, CDCl$_3$): d 1.99 (s, 2H, NH$_2$), 2.33 (s, 6H, CH$_3$), 3.93 (m, 2H, OCH$_2$), 4.51 (m, 1H, NCH), 6.99 (m, 1H, Ar), 7.07 (m, 2H, Ar), 7.35-7.44 (m, 3H, Ar), 7.52 (m, 2H, Ar); CNMR (100 MHz, CDCl$_3$): δ 16.4, 56.4, 77.8, 124.0, 126.0, 127.6, 128.5, 128.9, 130.9, 142.3, 155.5; GC-MS m/z 241.1 (M$^+$); Enantiomeric excess was determined by HPLC for acetyl derivative with a Chiralpak OD-H column (9:1 hexane: 2-propanol), 0.8 mL/min, 254 nm, minor enantiomer t$_R$=11.3 min, major enantiomer t$_R$=16.2 min.

(R)—N-[2-(2,6-Dimethyl-phenoxy)-1-methyl-ethyl]-acetamide (12b)

Purified by silica gel/hexane:ethyl acetate (1:1) column chromatography as a colorless oil; yield 84% (150 mg); 94% ee; $[α]^{20}_D$=−66 (c 1.0, CHCl$_3$); H NMR (400 MHz, CDCl$_3$): d 3.15 (d, 3H, J=6.8 Hz, CH$_3$), 2.08 (s, 3H, CH$_3$), 2.31 (s, 6H, CH$_3$), 3.75 (m, 1H, OCH$_2$), 3.86 (m, 1H, OCH$_2$), 4.41 (m, 1H, NCH), 5.95 (br, 1H, NH), 6.98 (m, 1H, Ar), 7.06 (m, 2H, Ar); CNMR (100 MHz, CDCl$_3$): δ 16.2, 17.8, 23.5, 45.5, 73.9, 124.2, 129.1, 130.7, 154.9, 169.4; GC-MS m/z 222.1 (M$^+$); Enantiomeric excess was determined by Chiral GC for acetyl derivative with a Chrompack Chiralsil-Dex-CB column (80° C., 2° C./min, to 140° C., remaining 80 min), major enantiomer t$_R$=89.4 min, minor enantiomer t$_R$=90.7 min.

(R)-2-(2,6-Dimethyl-phenoxy)-1-(4-fluoro-phenyl)-ethylamine (12c)

Purified by silica gel/hexane:ethyl acetate (2:1) column chromatography as a colorless oil; yield 89% (231 mg); 97% ee; $[α]^{20}_D$=−19 (c 1.9, CHCl$_3$); H NMR (400 MHz, CDCl$_3$): d 1.95 (s, 2H, NH$_2$), 2.31 (s, 6H, CH$_3$), 3.85 (m, 2H, OCH$_2$), 4.50 (m, 1H, NCH), 6.97 (m, 1H, Ar), 7.04-7.11 (m, 4H, Ar), 7.48 (m, 2H, Ar); CNMR (100 MHz, CDCl$_3$): δ 16.3, 55.7, 77.8, 115.2, 115.4, 124.0, 128.46, 128.54, 129.0, 130.8, 138.01, 138.04, 155.3, 161.0, 163.5; IR ν (cm$^{-1}$) 3036, 2922, 2865, 1603, 1508, 1475, 1441, 1377, 1263, 1221, 1199, 1156, 1090, 1010, 831, 767; GC-MS m/z 260.1 (M+H)$^+$; ESI HRMS m/z calcd for $C_{16}H_{19}FNO$ (M+H)$^+$ 260.14445, found 260.14434. Enantiomeric excess was determined by HPLC with a Chiralpak OD-H column (95:5 hexane: 2-propanol), 0.5 mL/min, 254 nm, minor enantiomer t$_R$=15.8 min, major enantiomer t$_R$=16.9 min.

(R)-1-(4-Fluoro-phenyl)-2-o-tolyloxy-ethylamine (12d)

Purified by silica gel/hexane:ethyl acetate (2:1) column chromatography as a colorless oil; yield 82% (201 mg); 92% ee; $[α]^{20}_D$=−47 (c 1.5, CHCl$_3$); H NMR (400 MHz, CDCl$_3$): d 1.90 (s, 2H, NH$_2$), 2.30 (s, 3H, CH$_3$), 3.98 (m, 1H, 00H$_2$), 4.11 (m, 1H, OCH$_2$), 4.50 (m, 1H, NCH), 6.83 (m, 1H, Ar), 6.93 (m, 1H, Ar), 7.11 (m, 2H, Ar), 7.21 (m, 2H, Ar), 7.51 (m, 2H, Ar); CNMR (100 MHz, CDCl$_3$): δ 16.3, 54.8, 73.9, 111.1, 115.3, 120.8, 126.8, 128.6, 130.8, 137.9, 156.7, 161.1, 163.5; IR ν (cm$^{-1}$) 3036, 2925, 2861, 1602, 1592, 1508, 1494, 1459, 1241, 1219, 1189, 1157, 1121, 1032, 832, 747, 712; GC-MS m/z 246.1 (M+H)$^+$; ESI HRMS m/z calcd for $C_{15}H_{17}FNO$ (M+H)$^+$ 246.12886, found 246.12869. Enantiomeric excess was determined by HPLC with a Chiralpak OD-H column (97:3 hexane: 2-propanol), 0.7 mL/min, 254 nm, major enantiomer t$_R$=18.5 min, minor enantiomer t$_R$=24.0 min.

(R)-1-(4-Chloro-phenyl)-2-o-tolyloxy-ethylamine (12e)

Purified by silica gel/hexane:ethyl acetate (2:1) column chromatography as a colorless oil; yield 73% (189 mg); 94% ee; $[α]^{20}_D$=−36 (c 1.2, CHCl$_3$); H NMR (400 MHz, CDCl$_3$): d 1.86 (s, 2H, NH$_2$), 2.29 (s, 3H, CH$_3$), 3.97 (m, 1H, OCH$_2$), 4.11 (m, 1H, OCH$_2$), 4.50 (m, 1H, NCH), 6.82 (m, 1H, Ar), 6.94 (m, 1H, Ar), 7.20 (m, 2H, Ar), 7.40 (m, 2H, Ar), 7.48 (m, 2H, Ar); CNMR (100 MHz, CDCl$_3$): δ 16.3, 54.9, 73.7, 111.1, 120.8, 126.7, 126.9, 128.4, 128.7, 130.8, 133.4, 140.7, 156.6; IR ν (cm$^{-1}$) 3024, 2920, 2865, 1599, 1590, 1492, 1459, 1240, 1190, 1121, 1090, 1048, 1032, 1013, 823, 747, 712; GC-MS m/z 262.1 (M+H)$^+$; ESI HRMS m/z calcd for C$_{15}$H$_{17}$ClNO (M+H)$^+$ 262.0993, found 262.09921. Enantiomeric excess was determined by HPLC with a Chiralpak OD-H column (96:4 hexane: 2-propanol), 0.9 mL/min, 254 nm, major enantiomer t$_R$=12.9 min, minor enantiomer t$_R$=18.0 min.

(R)-1-(4-Chloro-phenyl)-2-(2,6-dimethyl-phenoxy)-ethylamine (12f)

Purified by silica gel/hexane:ethyl acetate (2:1) column chromatography as a colorless oil; yield 85% (235 mg); 95% ee; [α]$^{20}_D$=−17 (c 1.0, CHCl$_3$); H NMR (400 MHz, CDCl$_3$): d 1.89 (s, 2H, NH$_2$), 2.29 (s, 6H, CH$_3$), 3.84 (m, 2H, OCH$_2$), 4.49 (m, 1H, NCH), 6.96 (m, 1H, Ar), 7.05 (m, 2H, Ar), 7.37 (m, 2H, Ar), 7.46 (m, 2H, Ar); CNMR (100 MHz, CDCl$_3$): δ 16.3, 55.8, 76.9, 124.0, 128.3, 128.6, 128.9, 130.8, 133.2, 140.8, 155.3; IR ν (cm$^{-1}$) 3024, 2921, 2857, 1599, 1492, 1468, 1263, 1198, 1089, 1010, 835, 823, 764, 702; GC-MS m/z 276.1 (M+H)$^+$; ESI HRMS m/z calcd for C$_{16}$H$_{19}$ClNO (M+H)$^+$ 276.11496, found 276.11465. Enantiomeric excess was determined by HPLC for acetyl derivative with a Chiralpak OD-H column (9:1 hexane: 2-propanol), 0.8 mL/min, 254 nm, minor enantiomer t$_R$=12.7 min, major enantiomer t$_R$=15.0 min.

(R)-2-(2-Chloro-phenoxy)-1-(4-chloro-phenyl)-ethylamine (12g)

Purified by silica gel/hexane:ethyl acetate (2:1) column chromatography as a colorless oil; yield 74% (208 mg); 92% ee; [α]$^{20}_D$=−43.5 (c 1.2, CHCl$_3$); H NMR (400 MHz, CDCl$_3$): d 1.93 (s, 2H, NH$_2$), 3.95 (m, 1H, OCH$_2$), 4.17 (m, 1H, OCH$_2$), 4.53 (m, 1H, NCH), 6.98 (m, 2H, Ar), 7.25 (m, 1H, Ar), 7.39 (m, 3H, Ar), 7.48 (m, 2H, Ar); CNMR (100 MHz, CDCl$_3$): δ 54.7, 74.8, 113.7, 121.9, 123.1, 127.8, 128.4, 128.7, 130.4, 133.5, 140.2, 154.1; IR ν (cm$^{-1}$) 3381, 2932, 2863, 1722, 1590, 1485, 1446, 1410, 1277, 1246, 1091, 1060, 1012, 955, 833, 821, 747; GC-MS m/z 281.9 (M+H)$^+$; ESI HRMS m/z calcd for C$_{14}$H$_{14}$Cl$_2$NO (M+H)$^+$ 282.04469, found 282.04456. Enantiomeric excess was determined by HPLC with a Chiralpak OD-H column (9:1 hexane: 2-propanol), 0.8 mL/min, 254 nm, major enantiomer t$_R$=12.1 min, minor enantiomer t$_R$=17.4 min.

(R)-1-Phenyl-2-o-tolyloxy-ethylamine (12h)

Purified by silica gel/hexane:ethyl acetate (2:1) column chromatography as a colorless oil; yield 91% (207 mg); 93% ee; [α]$^{20}_D$=−47 (c 2.4, CHCl$_3$); H NMR (400 MHz, CDCl$_3$): d 1.91 (s, 2H, NH$_2$), 2.33 (s, 3H, CH$_3$), 4.40 (m, 1H, OCH$_2$), 4.16 (m, 1H, OCH$_2$), 4.53 (m, 1H, NCH), 6.85-6.96 (m, 2H, Ar), 7.22 (m, 2H, Ar), 7.38 (m, 1H, Ar), 7.47 (m, 2H, Ar), 7.56 (m, 2H, Ar); CNMR (100 MHz, CDCl$_3$): δ 16.4, 55.5, 74.0, 111.2, 120.7, 126.8, 126.9, 127.0, 127.7, 128.6, 130.8, 142.2, 156.8; GC-MS m/z 226.9 (M$^i$); Enantiomeric excess was determined by HPLC for acetyl derivative with a Chiralpak OD-H column (9:1 hexane: 2-propanol), 0.8 mL/min, 254 nm, minor enantiomer t$_R$=18.9 min, major enantiomer t$_R$=22.4 min.

(R)-2-(4-Chloro-phenoxy)-1-phenyl-ethylamine (12i)

Purified by silica gel/hexane:ethyl acetate (2:1) column chromatography as a colorless oil; yield 89% (201 mg); 93% ee; [α]$^{20}_D$=−38 (c 1.2, CHCl$_3$); H NMR (400 MHz, CDCl$_3$): d 1.85 (s, 2H, NH$_2$), 3.95 (m, 1H, OCH$_2$), 4.10 (m, 1H, OCH$_2$), 4.48 (m, 1H, NCH), 6.88 (m, 2H, Ar), 7.27 (m, 2H, Ar), 7.35 (m, 1H, Ar), 7.40 (m, 2H, Ar), 7.48 (m, 2H, Ar); CNMR (100 MHz, CDCl$_3$): δ 55.2, 74.4, 115.9, 125.9, 126.9, 127.8, 128.7, 129.4, 141.7, 157.4; GC-MS m/z 248.1 (M$^+$); Enantiomeric excess was determined by HPLC with a Chiralpak OD-H column (96:4 hexane: 2-propanol), 0.9 mL/min, 254 nm, minor enantiomer t$_R$=15.1 min, major enantiomer t$_R$=20.1 min.

(R)-1-(2,3-Dihydro-benzo[1,4]dioxin-6-yl)-2-phenoxy-ethylamine (12j)

Purified by silica gel/hexane:ethyl acetate (1:1) column chromatography as a colorless oil; yield 83% (225 mg); 94% ee; [α]$^{20}_D$=−36 (c 1.0, CHCl$_3$); H NMR (400 MHz, CDCl$_3$): d 1.83 (s, 2H, NH$_2$), 3.91 (m, 1H, OCH$_2$), 4.11 (m, 1H, OCH$_2$), 4.31 (m, 4H OCH$_2$), 4.39 (m, 1H, NCH), 6.91-7.05 (m, 6H, Ar), 7.31 (m, 2H, Ar); CNMR (100 MHz, CDCl$_3$): δ 54.7, 64.4, 64.42, 74.0, 114.7, 115.8, 117.3, 119.9, 121.0, 129.5, 135.3, 143.1, 143.6, 158.8; GC-MS m/z 270.9 (M$^+$); Enantiomeric excess was determined by HPLC with a Chiralpak OD-H column (9:1 hexane: 2-propanol), 0.8 mL/min, 254 nm, major enantiomer t$_R$=28.2 min, minor enantiomer t$_R$=34.5 min.

(R)-1-(2,3-Dihydro-benzo[1,4]dioxin-6-yl)-2-o-tolyloxy-ethylamine (12k)

Purified by silica gel/hexane:ethyl acetate (1:1) column chromatography as a colorless oil; yield 86% (245 mg); 91% ee; [α]$^{20}_D$=−25 (c 1.2, CHCl$_3$); H NMR (400 MHz, CDCl$_3$): d 1.84 (s, 2H, NH$_2$), 2.31 (s, 3H, CH$_3$), 3.95 (m, 1H, OCH$_2$), 4.11 (m, 1H, OCH$_2$), 4.31 (m, 4H OCH$_2$), 4.41 (m, 1H, NCH), 6.84 (m, 1H, Ar), 6.90 (m, 2H, Ar), 6.97 (m, 1H, Ar), 7.05 (m, 1H, Ar), 7.18 (m, 2H, Ar); CNMR (100 MHz, CDCl$_3$): δ 16.3, 54.8, 64.41, 64.42, 74.0, 111.1, 115.8, 117.2, 119.9, 120.6, 126.7, 126.8, 130.7, 135.5, 143.0, 143.6, 156.8; IR ν (cm$^{-1}$) 3380, 3026, 2977, 2926, 2872, 1590, 1494, 1457, 1433, 1308, 1284, 1239, 1191, 1158, 1120, 1067, 1049, 1028, 925, 907, 885, 813, 749; GC-MS m/z 285.0 (Ie); ESI HRMS m/z calcd for C$_{17}$H$_{20}$NO$_3$ (M+H)$^+$ 286.14376, found 286.14355. Enantiomeric excess was determined by HPLC with a Chiralpak OD-H column (9:1 hexane: 2-propanol), 0.8 mL/min, 254 nm, major enantiomer t$_R$=21.5 min, minor enantiomer t$_R$=24.8 min.

(S)-2-(4-Methoxy-phenylsulfanyl)-1-phenyl-ethylamine (12l)

Purified by silica gel/hexane:ethyl acetate (1:1) column chromatography as a colorless oil; yield 86% (112 mg); 96% ee; [α]$^{20}_D$=+34.5 (c 1.3, CHCl$_3$); H NMR (400 MHz, CDCl$_3$): d 1.93 (s, 2H, NH$_2$), 2.97 (m, 1H, SCH$_2$), 3.24 (m, 1H, SCH$_2$), 3.86 (s, 3H, CH$_3$), 4.07 (m, 1H, NCH), 6.91 (m, 2H, Ar), 7.29-7.46 (m, 7H, Ar); CNMR (100 MHz, CDCl$_3$): δ 46.0, 54.6, 55.4, 114.8, 125.9, 126.5, 127.5, 128.6, 133.5, 144.4, 159.2; IR ν (cm$^{-1}$) 3365, 3024, 2910, 2835, 1591, 1570, 1491, 1454, 1283, 1241, 1175, 1103, 1028, 895, 823, 764, 698; GC-MS m/z 259.9 (De); ESI HRMS m/z calcd for C$_{15}$H$_{18}$NOS (M+H)$^+$ 260.11035, found 260.11044. Enantiomeric excess was determined by HPLC with a Chiralpak OD-H column (96:4 hexane: 2-propanol), 0.9 mL/min, 254 nm, minor enantiomer t$_R$=18.1 min, major enantiomer t$_R$=21.4 min.

(S)-1-(2,4-Difluorophenyl)-2-(4-methoxyphenylthio)ethanamine (12m)

Purified by silica gel/hexane:ethyl acetate (1:1) column chromatography as a colorless oil; yield 72% (212 mg); 94% ee; $[\alpha]^{20}_D = +26$ (c 1.2, CHCl$_3$); H NMR (400 MHz, CDCl$_3$): d 1.76 (s, 2H, NH$_2$), 2.97 (m, 1H, SCH$_2$), 3.26 (m, 1H, SCH$_2$), 3.86 (s, 3H, CH$_3$), 4.30 (m, 1H, NCH), 6.77 (m, 1H, Ar), 6.90 (m, 3H, Ar), 7.40-7.49 (m, 3H, Ar); CNMR (100 MHz, CDCl$_3$): δ 44.2, 48.5, 55.4, 103.8, 111.2, 114.7, 125.5, 127.0, 127.2, 128.7, 133.4, 159.2, 163.3; IR ν (cm$^{-1}$) 3367, 2939, 2838, 1593, 1572, 1493, 1463, 1426, 1282, 1242, 1174, 1134, 1092, 1029, 962, 849, 821, 735; GC-MS m/z 295.0 (M$^+$); ESI HRMS m/z calcd for C$_{15}$H$_{16}$F$_2$NOS (M+H)$^+$ 296.0915, found 296.09149. Enantiomeric excess was determined by HPLC with a Chiralpak OD-H column (96:4 hexane: 2-propanol), 0.9 mL/min, 254 nm, minor enantiomer t$_R$=14.8 min, major enantiomer t$_R$=18.8 min.

(R)-2-(3-(Benzyloxy)phenylthio)-1-(2,4-difluorophenyl)ethanamine (12n)

Purified by silica gel/hexane:ethyl acetate (1:1) column chromatography as a colorless oil; yield 66% (61 mg); 97% ee; $[\alpha]^{20}_D = -11$ (c 1.4, CHCl$_3$); H NMR (400 MHz, CDCl$_3$): d 1.80 (s, 2H, NH$_2$), 3.07 (m, 1H, SCH$_2$), 3.41 (m, 1H, SCH$_2$), 4.41 (m, 1H, NCH), 5.11 (s, 2H, OCH$_2$), 6.79-6.93 (m, 3H, Ar), 7.03 (m, 2H, Ar), 7.31 (m, 1H, Ar); 7.38-7.53 (m, 6H, Ar); CNMR (100 MHz, CDCl$_3$): δ 42.0, 48.5, 70.1, 103.6, 103.9, 104.1, 111.2, 111.3, 111.5, 113.1, 115.8, 122.0, 127.5, 128.1, 128.6, 128.8, 136.7, 136.8, 159.2; IR ν (cm$^{-1}$) 3373, 3066, 3028, 2921, 2873, 1585, 1572, 1498, 1476, 1453, 1425, 1378, 1276, 1224, 1134, 1093, 1024, 962, 848, 734, 697; ESI HRMS m/z calcd for C$_{21}$H$_{20}$F$_2$NOS (M+H)$^+$ 372.12281, found 372.12238. Enantiomeric excess was determined by HPLC with a Chiralpak OD-H column (96:4 hexane: 2-propanol), 0.9 mL/min, 254 nm, minor enantiomer t$_R$=26.2 min, major enantiomer t$_R$=29.0 min.

(R)-1-Phenyl-2-(pyridine-3-yloxy)ethanamine (12o)

After the mixture stirred for 48 h, 5 mL CH$_3$OH was added to quench the borane. The resulting mixture was refluxed overnight and then the solvents were removed under reduced pressure. The residue was purified by silica gel/CH$_2$Cl$_2$: MeOH (15:1) column chromatography and the correct product was obtained as a colorless oil; yield 83% (89 mg); 97% ee; $[\alpha]^{20}_D = -36$ (c 2.1, CHCl$_3$); H NMR (400 MHz, CDCl$_3$): d 1.92 (s, 2H, NH$_2$), 4.03 (m, 1H, OCH$_2$), 4.17 (m, 1H, OCH$_2$), 4.50 (m, 1H, NCH), 7.23 (m, 2H, Ar), 7.35-7.45 (m, 3H, Ar), 7.50 (m, 2H, Ar), 8.27 (m, 1H, Ar), 8.38 (m, 1H, Ar); CNMR (100 MHz, CDCl$_3$): δ 55.2, 74.3, 121.1, 123.8, 126.9, 127.9, 128.7, 138.2, 141.5, 142.5, 154.9; IR ν (cm$^{-1}$) 3365, 3278, 3030, 2924, 2865, 1574, 1475, 1453, 1425, 1264, 1230, 1188, 1103, 1049, 1011, 799, 760, 698; ESI HRMS m/z calcd for C$_{13}$H$_{15}$N$_2$O (M+H)$^+$ 215.11788, found 215.11736. Enantiomeric excess was determined by P NMR analysis of the phosphonate derivatives, which were prepared by the known method.

(R)-2-(6-Chloropyridin-2-yloxy)-1-phenylethanamine (12p)

After the mixture was stirred for 48 h, 5 mL CH$_3$OH was added to quench the borane. The resulting mixture was refluxed overnight and then the solvents were removed under reduced pressure. The residue was purified by silica gel/ hexane:ethyl acetate (1:1.5) column chromatography and the correct product was obtained as a white solid; mp 56-57° C.; yield 84% (208 mg); 96% ee; $[\alpha]^{20}_D = -23$ (c 3.5, CHCl$_3$); H NMR (400 MHz, CDCl$_3$): 1.81 (s, 2H, NH$_2$), 4.30 (m, 1H, NCH), 4.46-4.55 (m, 2H, OCH$_2$), 6.73 (m, 1H, Ar), 6.96 (m, 1H, Ar), 7.33-7.59 (m, 6H, Ar); CNMR (100 MHz, CDCl$_3$): δ 54.9, 72.4, 109.1, 116.6, 126.9, 127.7, 128.6, 140.7, 141.9, 148.4, 163.3; IR ν (cm$^{-1}$) 3344, 3264, 2939, 2864, 1591, 1561, 1494, 1458, 1432, 1407, 1387, 1359, 1330, 1296, 1262, 1160, 1075, 1045, 1003, 984, 941, 918, 868, 760, 728, 699; ESI HRMS m/z calcd for C$_{13}$H$_{14}$ClN$_2$O (M+H)$^+$ 249.07891, found 249.07862. Enantiomeric excess was determined by HPLC with a Chiralpak OD-H column (9:1 hexane: 2-propanol), 0.5 mL/min, 254 nm, minor enantiomer t$_R$=16.8 min, major enantiomer t$_R$=20.4 min.

In summary, the preparation of chiral mexiletine analogues, and novel β-thiophenoxy and pyridyl ethers was achieved by a facile four-step synthesis in good yield and excellent enantioselectivities. The highly enantioselective reduction of benzyloxime α-ethers, efficiently catalyzed by 10% of the novel spiroborate ester 6, is applicable for a wide range of other bioactive compounds. Considering the convenience and efficiency of this route, this methodology should open new avenues for further research.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

The invention claimed is:

1. A method of synthesizing enantiopure Mexiletine Analogues and Novel β-Thiophenoxy and Pyridyl ethers comprising: reducing an O-benzyl oxime having the formula I:

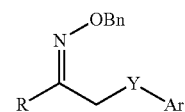

where R is a substituted or unsubstituted, alkyl, aryl group; Y is an oxygen atom or a sulfur atom and Ar is an aryl, alkyl, Pyridyl group; wherein said reduction is done in the presence of a catalyst agent having the formula II:

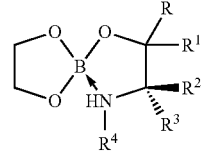

where, the R and R1 groups are equal or different; a hydrogen atom or a substituted or unsubstituted, aryl, alkyl, cycloalkyl or aralkyl; R2 and R3 groups are different; a hydrogen atom or a substituted or unsubstituted, alkyl, aryl, aralkyl group; and the R4 group is a H or a cycloalkyl or aralkyl group; and wherein the substituents R, R1, R2, R3, and R4 groups are substantially non-reactive.

2. The method of claim 1, wherein said O-benzyl oxime is reduced to form a mexiletine analogue having the formula III:

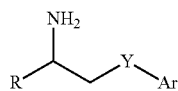

where, R is an aryl, alkyl group; Y is an oxygen atom or sulfur atom and Ar is an aryl, alkyl, Pyridyl group.

3. The method of claim 2, wherein said mexiletine analogue comprises:

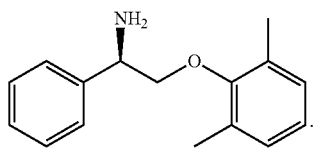

4. The method of claim 2, wherein said mexiletine analogue comprises:

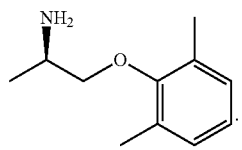

5. The method of claim 2, wherein said mexiletine analogue comprises:

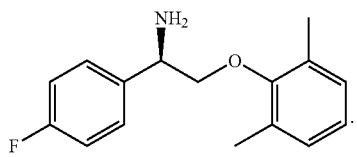

6. The method of claim 2, wherein said mexiletine analogue comprises:

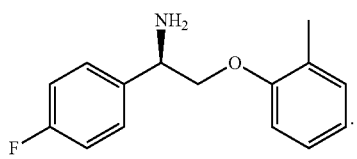

7. The method of claim 2, wherein said mexiletine analogue comprises:

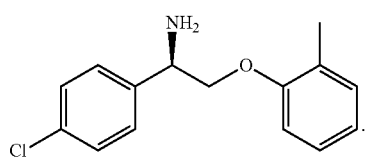

8. The method of claim 2, wherein said mexiletine analogue comprises:

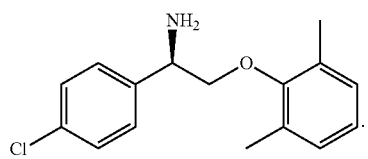

9. The method of claim 2, wherein said mexiletine analogue comprises:

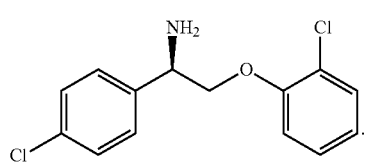

10. The method of claim 2, wherein said mexiletine analogue comprises:

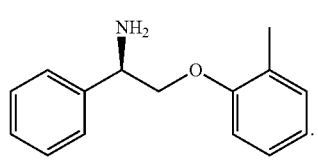

11. The method of claim 2, wherein said mexiletine analogue comprises:

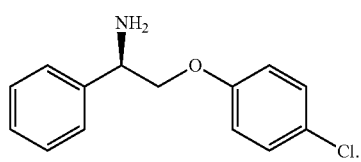

12. The method of claim 2, wherein said mexiletine analogue comprises:

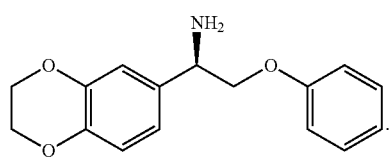

13. The method of claim 2, wherein said mexiletine analogue comprises:

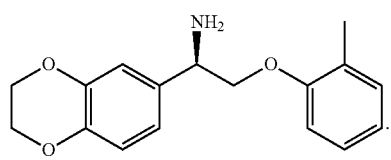

14. The method of claim 2, wherein said reduction produces an amine comprising:

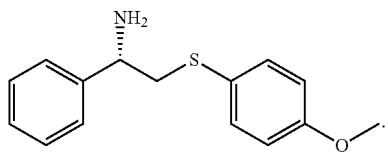

15. The method of claim 2, wherein said reduction produces an amine comprising:

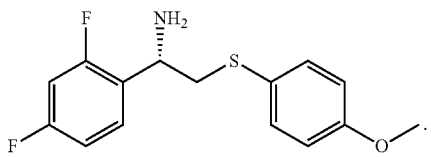

16. The method of claim 2, wherein said reduction produces an amine comprising:

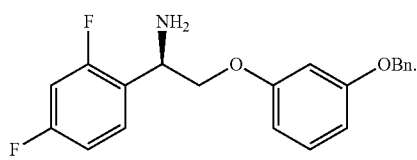

17. The method of claim 2, wherein said reduction produces an amine comprising:

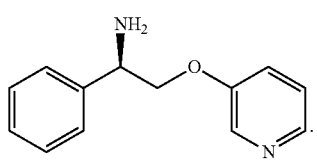

18. The method of claim 2, wherein said reduction produces an amine comprising:

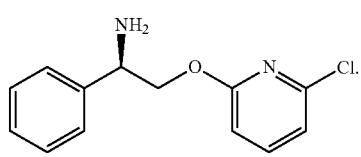

19. The method of claim 1, wherein said catalyst agent comprises:

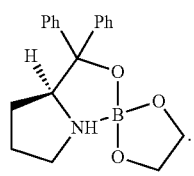

20. The method of claim 1, wherein said catalyst agent comprises:

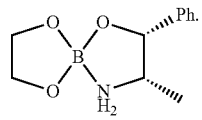

21. The method of claim 1, wherein said catalyst agent comprises:

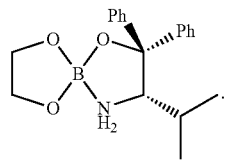

22. The method of claim 1, wherein said catalyst agent comprises:

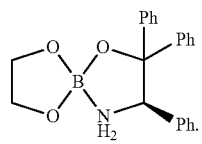

23. The method of claim 1, wherein said catalyst agent comprises:

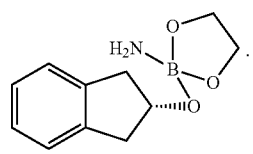

24. The method of claim 1, wherein the catalyst agent is able to reduce said oxime to obtain an enantioselectivity of at least 91%.

25. The method of claim 1, wherein the catalyst agent is able to reduce said oxime to obtain an enantioselectivity of from about 91% to about 97%.

26. The method of claim 1, comprising:
    adding anhydrous dioxane and BH3.THF in one portion to a reaction tube with said catalyst agent under $N_2$.

27. The method of claim 26, further comprising:
    stirring the mixture for a first period of time at a first predetermined temperature; and
    cooling said mixture at a second predetermined temperature.

28. The method of claim 27, further comprising:
    adding benzyl oxime in dioxane to the cooled mixture dropwise for a second period of time.

29. The method of claim 28, further comprising:
    stirring the resulting mixture at said second predetermined temperature until the conversion is completed.

30. The method of claim 26, wherein 10 mL of anhydrous dioxane and at least 4 mL of BH3.THF (1M in THF) in one portion are added to a reaction tube with 33 mg (0.1 mmol) of said catalyst agent under $N_2$.

31. The method of claim 27, wherein:
said first period of time is 1 hour;
said first predetermined temperature is about room temperature; and
said second predetermined temperature is about 0° C.

32. The method of claim 28, wherein 1 mmol of benzyl oxime in 5 ml of dioxane is added to the cooled mixture dropwise for about 1 hour.

33. The method of claim 29, wherein said second predetermined temperature is about 0° C. and said conversion is completed in about 48 hours.

* * * * *